United States Patent
Venuvenka et al.

(10) Patent No.: US 11,116,218 B2
(45) Date of Patent: Sep. 14, 2021

(54) ISOXAZOLE COMPOUND OR A SALT THEREOF

(71) Applicant: OAT AGRIO CO., LTD., Tokyo (JP)

(72) Inventors: Srinivas Venuvenka, Bhiwadi (IN); Rajesh Kumar Singh, Bhiwadi (IN); Ritesh Sharma, Bhiwadi (IN); Pitamber Swami, Bhiwadi (IN); Braj Bhushan Singh, Bhiwadi (IN); Manish Kumar Yadav, Bhiwadi (IN); Surendra Kumawat, Bhiwadi (IN); Manish K. Singh, Bhiwadi (IN)

(73) Assignee: OAT AGRIO CO., LTD., Tokyo (JP)

( * ) Notice: Subject to any disclaimer, the term of this patent is extended or adjusted under 35 U.S.C. 154(b) by 0 days.

(21) Appl. No.: 16/768,240

(22) PCT Filed: Nov. 29, 2018

(86) PCT No.: PCT/IB2018/059435
§ 371 (c)(1),
(2) Date: May 29, 2020

(87) PCT Pub. No.: WO2019/106584
PCT Pub. Date: Jun. 6, 2019

(65) Prior Publication Data
US 2020/0288717 A1    Sep. 17, 2020

(30) Foreign Application Priority Data
Nov. 30, 2017 (IN) .............................. 201711042933

(51) Int. Cl.
*C07D 261/08* (2006.01)
*A01N 43/80* (2006.01)

(52) U.S. Cl.
CPC ........... *A01N 43/80* (2013.01); *C07D 261/08* (2013.01)

(58) Field of Classification Search
CPC .................................................. C07D 261/08
See application file for complete search history.

(56) References Cited

U.S. PATENT DOCUMENTS

2002/0173424 A1    11/2002    Almsick

FOREIGN PATENT DOCUMENTS

| JP | 2008260706 | 10/2008 |
|---|---|---|
| JP | 2008308448 | 12/2008 |
| WO | WO1997046530 | 12/1997 |
| WO | WO2002018352 | 3/2002 |

OTHER PUBLICATIONS

Watanabe et al., "Synthesis of Arylisoxazolylphenylacetic acids and arylisoquinolinones and their plant grown regulating activities," Agricultural and Biological Chemistry, 50(10):2591-2595 (1986).

*Primary Examiner* — Shawquia Jackson
(74) *Attorney, Agent, or Firm* — Haley Guiliano LLP; James F. Haley, Jr.

(57) ABSTRACT

An object of the present invention is to provide an isoxazole compound or a salt thereof that controls pests.
The present invention provides an isoxazole compound represented by Formula (I):

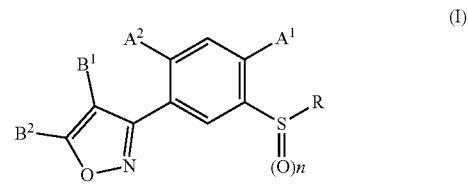

or a salt thereof,
wherein
R represents $C_{1-6}$ alkyl, or $C_{1-4}$ haloalkyl;
$A^1$ and $A^2$ are identical or different and each halogen or $C_{1-6}$ alkyl;
$B^1$ represents hydrogen, halogen or $C_{1-6}$ alkyl;
$B^2$ represents $C_{1-6}$ alkyl, $C_{1-4}$ haloalkyl, or substituted or unsubstituted aryl $C_{1-4}$ haloalkyl; and n represents an integer of 0 to 2.

28 Claims, No Drawings

ISOXAZOLE COMPOUND OR A SALT THEREOF

CROSS-REFERENCE TO RELATED APPLICATIONS

This application is a United States National Phase Application filed under 35 U.S.C. § 371 from International Patent Application No. PCT/IB2018/059435, filed on Nov. 29, 2018, which claims priority from Indian Patent Application No. 201711042933, filed on Nov. 30, 2017. The contents and disclosures of each of these applications are incorporated by reference herein in their entireties.

TECHNICAL FIELD

The present invention relates to a novel isoxazole compound or a salt.

BACKGROUND ART

In recent years, use of some insecticidal, miticidal or nematocidal agents is restricted due to environmental pollution and gradual accumulation of residual pesticides in the environment.

Due to the emergence of mites resistant to miticides in recent years as a result of long-term use of miticides, it has become difficult to accomplish control by use of known miticides. Therefore, it is urgent to develop novel miticides or nematocides which are thought to have different actions from commercially available miticides or nematocides.

For example, Patent literatures WO2002/018352 and WO97/046530 describe isoxazole derivatives substituted with phenyl groups. The 3-position of the phenyl group in the isoxazole derivative is restricted to the alkylsulfonyl group. The uses other than the herbicide are not disclosed at all in these patents.

The Agricultural and Biological Chemistry published in 1986 [50(10), 2591 (1986)] describes a plant growth regulating agent containing an isoxazole derivative substituted with a 3-methylthio group, but does not describe this isoxazole derivative as a pest controlling agent for agricultural and horticultural purposes.

Patent literature JP2008-308448A discloses a compound represented by the following formula (II):

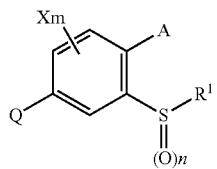

(II)

wherein $R^1$ represents alkyl, alkenyl or cycloalkyl; A represents halogen, alkyl, alkenyl, alkynyl, cycloalkyl, (hydroxyimino)methyl, (alkoxyimino)methyl, heteroaryl, or cyano; X represents halogen; m is an integer of 0 to 3; n is an integer of 0 to 1; and Q represents heteroaryl, or the like.

The above mentioned publication also discloses a compound represented by the following formula (III):

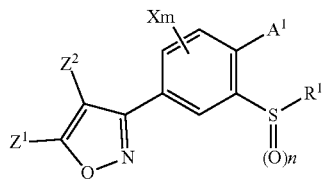

(III)

wherein $Z^1$ and $Z^2$ represent hydrogen, halogen, nitro, cyano, substituted or unsubstituted amino, substituted or unsubstituted alkyl, substituted or unsubstituted alkoxy, substituted or unsubstituted alkylthio, or the like; and $R^1$, A, X, m and n are as defined above.

The publication further discloses that the compounds represented by the formulas (II) and (III) exhibit miticidal activities and nematocidal activities.

However, examples in the same publication merely show that the compounds represented by the formulas (II) and (III) show the miticidal activity for the two-spotted spider mite and the citrus red mite in a high concentration of 300 ppm, but the effect on the eggs of mites have not been described.

In addition, although the compounds represented by the formula (III) in which n is 0 among the compounds represented by the formula (III) are particularly preferable, miticidal and ovicidal activities thereof are completely not sufficient.

CITATION LIST

Patent Literature

PLT 1 WO2002/018352
PLT 2 WP97/046530
PLT 3 JP2008-308448A

Non Patent Literature

NPLT 1 Agricultural and Biological Chemistry, 50(10), 2591 (1986)

SUMMARY OF THE INVENTION

Solution to Problem

The present invention provides an isoxazole compound or a salt thereof which has an excellent effect not only on adults of mites but also on eggs or ova.

The present invention also provides an isoxazole compound or a salt thereof which has an excellent controlling effect against mites and/or ova even when used at a low concentration.

The present invention further provides an isoxazole compound or a salt thereof having a high controlling effect on mites and/or ova which have acquired resistance to existing miticides.

The present invention also provides a miticide, an ovicide as well as a nematocide containing the above isoxazole compound or a salt thereof.

Specifically, as a result of extensive research, the present inventors have found that a compound represented by the following general formula (I) or a salt thereof exhibits excellent miticidal activity at low concentration. At the same time, the compound represented by the formula (I) also exhibits ovicidal activity against pests for agricultural and horticultural use, particularly against mites typified by the two-spotted spider mite, the citrus red mite and Kanzawa spider mite. Furthermore, it was found that the compound represented by the formula (I) has extremely excellent nematocidal activity at low concentrations against nematodes such as root-knot nematode, root-lesion nematode and the like, and the present invention has been completed.

Thus, the present invention relates to a novel isoxazole compound represented by the following formula (I) or a salt thereof.

More specifically, the present invention includes the following embodiments:

Item 1:

An isoxazole compound is represented by Formula (I):

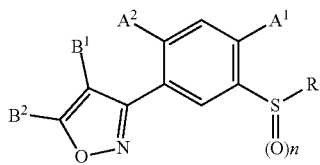

or a salt thereof,
wherein
R represents $C_{1-6}$ alkyl, or $C_{1-4}$ haloalkyl;
$A^1$ and $A^2$ are identical or different and each halogen or $C_{1-6}$ alkyl;
$B^1$ represents hydrogen, halogen or $C_{1-6}$ alkyl;
$B^2$ represents $C_{1-6}$ alkyl, $C_{1-4}$ haloalkyl, or substituted or unsubstituted aryl $C_{1-4}$ haloalkyl; and n represents an integer of 0 to 2.

Item 2:

An isoxazole compound or a salt thereof according to item 1, wherein R is normal propyl or 2,2,2-trifluoroethyl.

Item 3:

An isoxazole compound or a salt thereof according to any one of item 1 or 2, wherein $A^1$ is fluorine, chlorine, or methyl.

Item 4:

An isoxazole compound or a salt thereof according to any one of items 1 to 3, wherein $A^2$ is fluorine, chlorine, or methyl.

Item 5:

An isoxazole compound or a salt thereof according to any one of items 1 to 4, wherein $B^1$ is hydrogen or methyl.

Item 6:

An isoxazole compound or a salt thereof according to any one of items 1 to 5, wherein $B^2$ is difluoromethyl, trifluoromethyl, chlorodifluoromethyl, pentafluoroethyl, heptafluoropropyl or difluoro(phenyl)methyl.

Item 7:

An isoxazole compound or a salt thereof according to any one of items 1 to 6, wherein n is an integer of 0 or 1.

Item 8:

An isoxazole compound or a salt thereof according to item 1, which is selected from the group consisting of:
3-(2-fluoro-4-methyl-5-((2,2,2-trifluoroethyl)sulfinyl)phenyl)-5-(trifluoromethyl)isoxazole;
3-(2-fluoro-4-methyl-5-((2,2,2-trifluoroethyl)sulfinyl)phenyl)-5-(heptafluoropropyl)isoxazole;
5-(difluoromethyl)-3-(2-fluoro-4-methyl-5-((2,2,2-trifluoroethyl)thio)phenyl)isoxazole;
5-(chlorodifluoromethyl)-3-(2-fluoro-4-methyl-5-((2,2,2-trifluoroethyl)sulfinyl)phenyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole;
3-(2,4-dimethyl-5-((2,2,2-trifluoroethyl)sulfinyl)phenyl)-5-(trifluoromethyl)isoxazole;
3-(2-fluoro-4-methyl-5-(propylsulfinyl)phenyl)-5-(trifluoromethyl)isoxazole;
3-(2-fluoro-4-methyl-5-((2,2,2-trifluoroethyl)sulfinyl)phenyl)-4-methyl-5-(trifluoromethyl)isoxazole;
3-(2-chloro-4-methyl-5-((2,2,2-trifluoroethyl)thio)phenyl)-5-(chlorodifluoromethyl)isoxazole;
3-(2-chloro-4-methyl-5-((2,2,2-trifluoroethyl)sulfinyl)phenyl)-5-(chlorodifluoromethyl)isoxazole;
5-(difluoromethyl)-3-(2,4-dimethyl-5-((2,2,2-trifluoroethyl)thio)phenyl)isoxazole;
5-(difluoromethyl)-3-(2,4-dimethyl-5-((2,2,2-trifluoroethyl)sulfinyl)phenyl)isoxazole;
5-(chlorodifluoromethyl)-3-(2,4-dimethyl-5-((2,2,2-trifluoroethyl)thio)phenyl)isoxazole;
5-(chlorodifluoromethyl)-3-(2,4-dimethyl-5-((2,2,2-trifluoroethyl)sulfinyl)phenyl)isoxazole;
3-(2-chloro-4-methyl-5-((2,2,2-trifluoroethyl)thio)phenyl)-5-(difluoro(phenyl)methyl)isoxazole;
3-(2-chloro-4-methyl-5-((2,2,2-trifluoroethyl)sulfinyl)phenyl)-5-(difluoro(phenyl)methyl)isoxazole;
3-(2-chloro-4-methyl-5-((2,2,2-trifluoroethyl)thio)phenyl)-5-(difluoromethyl)isoxazole; and 3-(2-chloro-4-methyl-5-((2,2,2-trifluoroethyl)sulfinyl)phenyl)-5-(difluoromethyl)isoxazole.

Item 9:

An isoxazole compound or a salt thereof according to item 1, which is selected from the group consisting of:
3-(2-fluoro-4-methyl-5-((2,2,2-trifluoroethyl)sulfinyl)phenyl)-5-(trifluoromethyl)isoxazole;
3-(2-fluoro-4-methyl-5-((2,2,2-trifluoroethyl)sulfinyl)phenyl)-5-(heptafluoropropyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole;
3-(2-fluoro-4-methyl-5-(propylsulfinyl)phenyl)-5-(trifluoromethyl)isoxazole;
3-(2-fluoro-4-methyl-5-((2,2,2-trifluoroethyl)sulfinyl)phenyl)-4-methyl-5-(trifluoromethyl)isoxazole;
3-(2-chloro-4-methyl-5-((2,2,2-trifluoroethyl)thio)phenyl)-5-(chlorodifluoromethyl)isoxazole;
3-(2-chloro-4-methyl-5-((2,2,2-trifluoroethyl)sulfinyl)phenyl)-5-(chlorodifluoromethyl)isoxazole;
3-(2-chloro-4-methyl-5-((2,2,2-trifluoroethyl)thio)phenyl)-5-(difluoromethyl)isoxazole; and
3-(2-chloro-4-methyl-5-((2,2,2-trifluoroethyl)sulfinyl)phenyl)-5-(difluoromethyl)isoxazole.

Item 10:

An isoxazole compound or a salt thereof according to item 1, which is selected from the group consisting of:
3-(2-fluoro-4-methyl-5-((2,2,2-trifluoroethyl)sulfinyl)phenyl)-5-(trifluoromethyl)isoxazole;
5-(chlorodifluoromethyl)-3-(2-fluoro-4-methyl-5-((2,2,2-trifluoroethyl)sulfinyl)phenyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole;
3-(2-fluoro-4-methyl-5-(propylsulfinyl)phenyl)-5-(trifluoromethyl)isoxazole;

3-(2-fluoro-4-methyl-5-((2,2,2-trifluoroethyl)sulfinyl)
phenyl)-4-methyl-5-(trifluoromethyl)isoxazole;
3-(2-chloro-4-methyl-5-((2,2,2-trifluoroethyl)thio)phe-
nyl)-5-(chlorodifluoromethyl)isoxazole;
3-(2-chloro-4-methyl-5-((2,2,2-trifluoroethyl)sulfinyl)
phenyl)-5-(chlorodifluoromethyl)isoxazole;
3-(2-chloro-4-methyl-5-((2,2,2-trifluoroethyl)thio)phe-
nyl)-5-(difluoromethyl)isoxazole; and
3-(2-chloro-4-methyl-5-((2,2,2-trifluoroethyl)sulfinyl)
phenyl)-5-(difluoromethyl)isoxazole.

Item 11:
An isoxazole compound or a salt thereof according to item 1, which is selected from the group consisting of:
3-(2-fluoro-4-methyl-5-((2,2,2-trifluoroethyl)sulfinyl)
phenyl)-5-(trifluoromethyl)isoxazole;
5-(difluoro(phenyl)methyl)-3-(2-fluoro-4-methyl-5-((2,2,
2-trifluoroethyl)thio)phenyl)isoxazole;
3-(2-chloro-4-methyl-5-((2,2,2-trifluoroethyl)sulfinyl)
phenyl)-5-(trifluoromethyl)isoxazole;
3-(2-fluoro-4-methyl-5-(propylsulfinyl)phenyl)-5-(trif-
luoromethyl)isoxazole;
3-(2-fluoro-4-methyl-5-((2,2,2-trifluoroethyl)sulfinyl)
phenyl)-4-methyl-5-(trifluoromethyl)isoxazole;
3-(2-chloro-4-methyl-5-((2,2,2-trifluoroethyl)thio)phe-
nyl)-5-(chlorodifluoromethyl)isoxazole;
3-(2-chloro-4-methyl-5-((2,2,2-trifluoroethyl)sulfinyl)
phenyl)-5-(chlorodifluoromethyl)isoxazole;
3-(2-chloro-4-methyl-5-((2,2,2-trifluoroethyl)thio)phe-
nyl)-5-(difluoromethyl)isoxazole; and
3-(2-chloro-4-methyl-5-((2,2,2-trifluoroethyl)sulfinyl)
phenyl)-5-(difluoromethyl)isoxazole.

Item 12:
A pest controlling agent comprising the isoxazole compound or a salt thereof as an active ingredient according to any one of items 1 to 11.

Item 12-1:
A miticide comprising the isoxazole compound or a salt thereof as an active ingredient according to any one of items 1 to 11.

Item 12-2:
A nematocide comprising the isoxazole compound or a salt thereof as an active ingredient according to any one of items 1 to 11.

Item 13:
An agricultural composition comprising the isoxazole compound or a salt thereof according to any one of items 1 to 11.

Item 14:
A composition for controlling a pest, comprising the isoxazole compound or a salt thereof according to any one of items 1 to 11.

Item 15:
A miticidal composition comprising the isoxazole compound or a salt thereof according to any one of items 1 to 11.

Item 16:
An ovicidal composition comprising the isoxazole compound or a salt thereof according to any one of items 1 to 11.

Item 17:
A nematocidal composition comprising the isoxazole compound or a salt thereof according to any one of items 1 to 11.

Item 18:
A composition for controlling a mite, comprising the isoxazole compound or a salt thereof according to any one of items 1 to 11.

Item 19:
A composition for controlling an egg or ovum, comprising the isoxazole compound or a salt thereof according to any one of items 1 to 11.

Item 20:
A composition for controlling a nematode, comprising the isoxazole compound or a salt thereof according to any one of items 1 to 11.

Item 21:
A composition for use in controlling a mite, comprising the isoxazole compound or a salt thereof according to any one of items 1 to 11.

Item 22:
A composition for use in controlling an egg or ovum, comprising the isoxazole compound or a salt thereof according to any one of items 1 to 11.

Item 23:
A composition for use in controlling a nematode, comprising the isoxazole compound or a salt thereof according to any one of items 1 to 11.

Item 24:
A method for using the isoxazole compound or a salt thereof according to any one of Items 1 to 11 for controlling pests.

Item 24-1:
A method for using the isoxazole compound or a salt thereof according to any one of Items 1 to 11 for controlling mites.

Item 24-2:
A method for using the isoxazole compound or a salt thereof according to any one of Items 1 to 11 for controlling nematodes.

Item 25:
A method for controlling pests, which comprises applying the isoxazole compound or a salt thereof according to any one of items 1 to 11 to a plant or its vicinity, or soil where a plant is cultivated.

Item 25-1:
A method for controlling mites, which comprises applying the isoxazole compound or a salt thereof according to any one of items 1 to 11 to a plant or its vicinity, or soil where a plant is cultivated.

Item 25-2:
A method for controlling nematodes, which comprises applying the isoxazole compound or a salt thereof according to any one of items 1 to 11 to a plant or its vicinity, or soil where a plant is cultivated.

Item 26:
A method for controlling pests, which comprises applying an effective amount of the isoxazole compound or a salt thereof according to any one of items 1 to 11 to pests, a habitat of pests, or a place where inhabitation is predicted.

Item 26-1:
A method for controlling mites, which comprises applying an effective amount of the isoxazole compound or a salt thereof according to any one of items 1 to 11 to mite, a habitat of mites, or a place where inhabitation is predicted.

Item 26-2:
A method for controlling nematodes, which comprises applying an effective amount of the isoxazole compound or a salt thereof according to any one of items 1 to 11 to nematode, a habitat of nematodes, or a place where inhabitation is predicted.

Item 27:
A method for killing a mite, which comprises applying the isoxazole compound or a salt thereof according to any one of items 1 to 11 to a plant or its vicinity, or soil where a plant is cultivated.

Item 28:

A method for killing a mite, which comprises applying an effective amount of the isoxazole compound or a salt thereof according to any one of items 1 to 11 to a mite, a habitat of mites, or a place where inhabitation is predicted.

Item 29:

A method for killing an ovum, which comprises applying the isoxazole compound or a salt thereof according to any one of items 1 to 11 to a plant or its vicinity, or soil where a plant is cultivated.

Item 30:

A method for killing an ovum, which comprises applying an effective amount of the isoxazole compound or a salt thereof according to any one of items 1 to 11 to an ovum or a place where oviposition is predicted.

Item 31:

A method for killing a nematode, which comprises applying the isoxazole compound or a salt thereof according to any one of items 1 to 11 to a plant or its vicinity, or soil where a plant is cultivated.

Item 32:

A method for killing a nematode, which comprises applying an effective amount of the isoxazole compound or a salt thereof according to any one of items 1 to 11 to a nematode, a habitat of nematodes, or a place where inhabitation of a nematode is predicted.

Item 33:

A use of the isoxazole compound or a salt thereof according to any one of items 1 to 11 as a miticidal agent.

Item 34:

A use as a miticidal agent of an isoxazole compound selected from the group consisting of:
- 3-(2-fluoro-4-methyl-5-((2,2,2-trifluoroethyl)sulfinyl) phenyl)-5-(trifluoromethyl)isoxazole;
- 3-(2-fluoro-4-methyl-5-((2,2,2-trifluoroethyl)sulfinyl) phenyl)-5-(heptafluoropropyl)isoxazole;
- 5-(difluoro(phenyl)methyl)-3-(2-fluoro-4-methyl-5-((2,2,2-trifluoroethyl)thio)phenyl)isoxazole;
- 3-(2-chloro-4-methyl-5-((2,2,2-trifluoroethyl)sulfinyl) phenyl)-5-(trifluoromethyl)isoxazole;
- 3-(2-fluoro-4-methyl-5-(propylsulfinyl)phenyl)-5-(trifluoromethyl)isoxazole;
- 3-(2-fluoro-4-methyl-5-((2,2,2-trifluoroethyl)sulfinyl) phenyl)-4-methyl-5-(trifluoromethyl)isoxazole;
- 3-(2-chloro-4-methyl-5-((2,2,2-trifluoroethyl)thio)phenyl)-5-(chlorodifluoromethyl)isoxazole;
- 3-(2-chloro-4-methyl-5-((2,2,2-trifluoroethyl)sulfinyl) phenyl)-5-(chlorodifluoromethyl)isoxazole;
- 3-(2-chloro-4-methyl-5-((2,2,2-trifluoroethyl)thio)phenyl)-5-(difluoromethyl)isoxazole; and
- 3-(2-chloro-4-methyl-5-((2,2,2-trifluoroethyl)sulfinyl) phenyl)-5-(difluoromethyl)isoxazole, or a salt thereof.

Item 35:

A use of the isoxazole compound or a salt thereof according to any one of items 1 to 11 as an ovicidal agent.

Item 36:

A use as an ovicidal agent of an isoxazole compound selected from the group consisting of:
- 3-(2-fluoro-4-methyl-5-((2,2,2-trifluoroethyl)sulfinyl) phenyl)-5-(trifluoromethyl)isoxazole;
- 5-(chlorodifluoromethyl)-3-(2-fluoro-4-methyl-5-((2,2,2-trifluoroethyl)sulfinyl)phenyl)isoxazole;
- 5-(difluoro(phenyl)methyl)-3-(2-fluoro-4-methyl-5-((2,2,2-trifluoroethyl)thio)phenyl)isoxazole;
- 3-(2-chloro-4-methyl-5-((2,2,2-trifluoroethyl)sulfinyl) phenyl)-5-(trifluoromethyl)isoxazole;
- 3-(2-fluoro-4-methyl-5-(propylsulfinyl)phenyl)-5-(trifluoromethyl)isoxazole;
- 3-(2-fluoro-4-methyl-5-((2,2,2-trifluoroethyl)sulfinyl) phenyl)-4-methyl-5-(trifluoromethyl)isoxazole;
- 3-(2-chloro-4-methyl-5-((2,2,2-trifluoroethyl)thio)phenyl)-5-(chlorodifluoromethyl)isoxazole;
- 3-(2-chloro-4-methyl-5-((2,2,2-trifluoroethyl)sulfinyl) phenyl)-5-(chlorodifluoromethyl)isoxazole;
- 3-(2-chloro-4-methyl-5-((2,2,2-trifluoroethyl)thio)phenyl)-5-(difluoromethyl)isoxazole; and
- 3-(2-chloro-4-methyl-5-((2,2,2-trifluoroethyl)sulfinyl) phenyl)-5-(difluoromethyl)isoxazole, or a salt thereof.

Item 37:

A use of the isoxazole compound or a salt thereof according to any one of items 1 to 11 as a nematocidal agent.

Item 38:

A use as a nematocidal agent of an isoxazole compound selected from the group consisting of:
- 3-(2-fluoro-4-methyl-5-((2,2,2-trifluoroethyl)sulfinyl) phenyl)-5-(trifluoromethyl)isoxazole;
- 3-(2-fluoro-4-methyl-5-((2,2,2-trifluoroethyl)sulfinyl) phenyl)-5-(perfluoroethyl)isoxazole;
- 3-(2-fluoro-4-methyl-5-((2,2,2-trifluoroethyl)sulfonyl) phenyl)-5-(perfluoropropyl)isoxazole;
- 3-(2-fluoro-4-methyl-5-((2,2,2-trifluoroethyl)thio)phenyl)-5-(perfluorobutyl)isoxazole;
- 5-(difluoromethyl)-3-(2-fluoro-4-methyl-5-((2,2,2-trifluoroethyl)thio)phenyl)isoxazole;
- 5-(difluoromethyl)-3-(2-fluoro-4-methyl-5-((2,2,2-trifluoroethyl)sulfinyl)phenyl)isoxazole;
- 5-(chlorodifluoromethyl)-3-(2-fluoro-4-methyl-5-((2,2,2-trifluoroethyl)sulfinyl)phenyl)isoxazole;
- 5-(difluoro(phenyl)methyl)-3-(2-fluoro-4-methyl-5-((2,2,2-trifluoroethyl)thio)phenyl)isoxazole;
- 5-(difluoro(phenyl)methyl)-3-(2-fluoro-4-methyl-5-((2,2,2-trifluoroethyl)sulfinyl)phenyl)isoxazole;
- 3-(2-chloro-4-methyl-5-((2,2,2-trifluoroethyl)sulfinyl) phenyl)-5-(trifluoromethyl)isoxazole;
- 3-(2,4-dimethyl-5-((2,2,2-trifluoroethyl)thio)phenyl)-5-(trifluoromethyl)isoxazole;
- 3-(2,4-dimethyl-5-((2,2,2-trifluoroethyl)sulfonyl)phenyl)-5-(trifluoromethyl)isoxazole;
- 3-(2,4-difluoro-5-((2,2,2-trifluoroethyl)sulfinyl)phenyl)-5-(trifluoromethyl)isoxazole;
- 3-(2,4-dichloro-5-((2,2,2-trifluoroethyl)thio)phenyl)-5-(trifluoromethyl)isoxazole;
- 3-(2-fluoro-4-methyl-5-(propylsulfinyl)phenyl)-5-(trifluoromethyl)isoxazole;
- 3-(2-fluoro-4-methyl-5-((2,2,2-trifluoroethyl)sulfinyl) phenyl)-4-methyl-5-(trifluoromethyl)isoxazole;
- 5-(difluoro(phenyl)methyl)-3-(2,4-dimethyl-5-((2,2,2-trifluoroethyl)thio)phenyl)isoxazole;
- 3-(2-chloro-4-methyl-5-((2,2,2-trifluoroethyl)thio)phenyl)-5-(chlorodifluoromethyl)isoxazole;
- 3-(2-chloro-4-methyl-5-((2,2,2-trifluoroethyl)sulfinyl) phenyl)-5-(chlorodifluoromethyl)isoxazole;
- 5-(difluoromethyl)-3-(2,4-dimethyl-5-((2,2,2-trifluoroethyl)thio)phenyl)isoxazole;
- 5-(chlorodifluoromethyl)-3-(2,4-dimethyl-5-((2,2,2-trifluoroethyl)thio)phenyl)isoxazole;
- 5-(chlorodifluoromethyl)-3-(2,4-dimethyl-5-((2,2,2-trifluoroethyl)sulfinyl)phenyl)isoxazole;
- 3-(2-chloro-4-methyl-5-((2,2,2-trifluoroethyl)thio)phenyl)-5-(difluoromethyl)isoxazole; and
- 3-(2-chloro-4-methyl-5-((2,2,2-trifluoroethyl)sulfinyl) phenyl)-5-(difluoromethyl)isoxazole; or a salt thereof.

It is intended that one or more of the aforementioned features can be provided as a combination of one or more of the aforementioned features in addition to as the explicitly shown combinations. Further embodiments and advantages of the present invention are recognized by those skilled in the art by reading and understanding the following Detailed Description as needed.

Advantageous Effects of Invention

According to the present invention, it is possible to provide an isoxazole compound or a salt thereof having an excellent controlling effect against pests.

Especially, according to the present invention, the isoxazole compound or a salt thereof having an excellent effect not only on adults of mites but also on eggs even at low concentrations and a miticide containing these compounds can be provided.

Additionally, with the present invention, the isoxazole compound or a salt thereof having a high controlling effect in a mite which has acquired resistance to an existing miticide and a miticide containing these compounds can be provided.

In addition, the isoxazole compound or a salt thereof of the present invention has an excellent controlling effect on nematodes and a nematocide containing these compounds can be provided.

DESCRIPTION OF EMBODIMENTS

Hereinafter, the present invention will be described in more details with reference to examples, but the technical scope of the present invention is not limited to these examples.

Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

An isoxazole compound or a salt thereof

The present invention provides an isoxazole compound or a salt thereof represented by Formula (I):

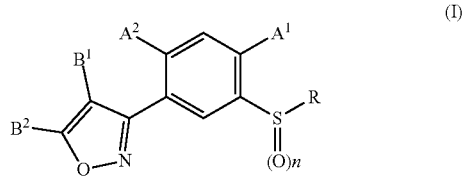

wherein R, $A^1$, $A^2$, $B^1$, $B^2$ and n are as defined above.

The following shows specific examples of each group as used in this specification.

The term "unsubstituted" in this description means that a base group is the only group constituting the group. In addition, unless specifically indicated otherwise, a group has the meaning of being "unsubstituted" when the group is not described as being "substituted" and described using the name of the base group.

On the other hand, the term "substituted" means that any of hydrogen atoms of the base group are substituted with a group that is the same as or different from the base group. The "substituted" group may be substituted with one substituent, or two or more substituents. The two or more substituents may be the same or different.

The "substituent" is not particularly limited as long as it is chemically permissible and achieves the effects of the present invention.

Examples of the "substituent" include a halogen atom such as a fluorine atom, chlorine atom, bromine atom, iodine atom or the like; a $C_{1-6}$ alkyl such as a methyl, ethyl, n-propyl, isopropyl, n-butyl, s-butyl, isobutyl, t-butyl, n-pentyl, n-hexyl or the like; a $C_{3-8}$ cycloalkyl such as a cyclopropyl, cyclobutyl, cyclopentyl, cyclohexyl, cycloheptyl or the like; a $C_{2-6}$ alkenyl such as a vinyl, 1-propenyl, 2-propenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl, 5-hexenyl or the like; a $C_{3-8}$ cycloalkenyl such as a 2-cyclopropenyl, 2-cyclopentenyl, 3-cyclohexenyl, 4-cyclooctenyl or the like; a $C_{2-6}$ alkynyl such as an ethynyl, 1-propynyl, 2-propynyl, 1-butynyl, 2-butynyl, 3-butynyl, 1-methyl-2-propynyl, 2-methyl-3-butynyl, 1-pentynyl, 2-pentynyl, 3-pentynyl, 4-pentynyl, 1-methyl-2-butynyl, 2-methyl-3-pentynyl, 1-hexynyl, 1,1-dimethyl-2-butynyl or the like; a $C_{1-6}$ alkoxy such as a methoxy, ethoxy, n-propoxy, isopropoxy, n-butoxy, s-butoxy, isobutoxy, t-butoxy or the like; a $C_{2-6}$ alkenyloxy such as a vinyloxy, allyloxy, propenyloxy, butenyloxy or the like; a $C_{2-6}$ alkynyloxy such as an ethynyloxy, propargyloxy or the like; a $C_{6-10}$ aryl such as a phenyl, naphthyl or the like; a $C_{6-10}$ aryloxy such as a phenoxy, 1-naphthoxy or the like; a $C_{7-11}$ aralkyl such as a benzyl, phenethyl or the like; a $C_{7-11}$ aralkyloxy such as a benzyloxy, phenethyloxy or the like; a $C_{1-7}$ acyl such as a formyl, acetyl, propionyl, benzoyl, cyclohexyl carbonyl or the like; a $C_{1-7}$ acyloxy such as a formyloxy, acetyloxy, propionyloxy, benzoyloxy, cyclohexyl carbonyloxy or the like; a $C_{1-6}$ alkoxycarbonyl such as a methoxycarbonyl, ethoxycarbonyl, n-propoxycarbonyl, isopropoxycarbonyl, n-butoxycarbonyl, t-butoxycarbonyl or the like; a carboxyl; a hydroxy; an oxo; a $C_{1-6}$ haloalkyl such as a chloromethyl, chloroethyl, trifluoromethyl, 1,2-dichloro-n-propyl, 1-fluoro-n-butyl, perfluoro-n-pentyl or the like; a $C_{2-6}$ haloalkenyl such as a 2-chloro-1-propenyl, 2-fluoro-1-butenyl or the like; a $C_{2-6}$ haloalkynyl such as a 4,4-dichloro-1-butynyl, 4-fluoro-1-pentynyl, 5-bromo-2-pentynyl or the like; a $C_{1-6}$ haloalkoxy such as a 2-chloro-n-propoxy, 2,3-dichlorobutoxy or the like; a $C_{2-6}$ haloalkenyloxy such as a 2-chloropropenyloxy, 3-bromobutenyloxy or the like; a $C_{6-10}$ haloaryl such as a 4-chlorophenyl, 4-fluorophenyl, 2,4-dichlorophenyl or the like; a $C_{6-10}$ haloaryloxy such as a 4-fluorophenyloxy, 4-chloro-1-naphthoxy or the like; a halogen-substituted $C_{1-7}$ acyl such as a chloroacetyl, trifluoroacetyl, trichloroacetyl, 4-chlorobenzoyl or the like; a cyano; an isocyano; a nitro; an isocyanato; a cyanato; an amino; a $C_{1-6}$ alkyl amino such as a methyl amino, dimethyl amino, diethyl amino or the like; a $C_{6-10}$ aryl amino such as an anilino, naphthyl amino or the like; a $C_{7-11}$ aralkyl amino such as a benzyl amino, phenyl ethyl amino or the like; a $C_{1-7}$ acyl amino such as a formyl amino, acetyl amino, propanoyl amino, butyryl amino, isopropyl carbonyl amino, benzoyl amino or the like; a $C_{1-6}$ alkoxycarbonyl amino such as a methoxycarbonyl amino, ethoxycarbonyl amino, n-propoxycarbonyl amino, isopropoxycarbonyl amino or the like; an unsubstituted or substituted aminocarbonyl such as an aminocarbonyl, dimethyl aminocarbonyl, phenyl aminocarbonyl, N-phenyl-N-methyl aminocarbonyl or the like; an imino-substituted $C_{1-6}$ alkyl such as an iminomethyl, (1-imino)ethyl, (1-imino)-n-propyl or the like; a hydroxyimino-substituted $C_{1-6}$ alkyl such as a hydroxyiminomethyl, (1-hydroxyimino)ethyl, (1-hydroxyimino)propyl, methoxyiminomethyl, (1-methoxyimino)ethyl or the like; a mercapto; an isothiocyanato; a thiocyanato; a $C_{1-6}$ alkylthio such as a methylthio, ethylthio, n-propylthio, isopropylthio, n-butylthio, isobutylthio, s-butylthio, t-butylthio or the like; a $C_{2-6}$ alkenylthio such as a vinylthio, allylthio or the like; a $C_{2-6}$ alkynylthio such as an ethynylthio, propargylthio or the like; a $C_{6-10}$ arylthio such as a phenylthio, naphthylthio or the like; a heterocyclylthio such as a thiazolylthio, pyridylthio or the like; a $C_{7-11}$ aralkylthio such as a benzylthio, phenethylthio or the like; a ($C_{1-6}$ alkylthio)carbonyl such as a (methylthio)carbonyl, (ethylthio)carbonyl, (n-propylthio)carbonyl, (isopropylthio)carbonyl, (n-butylthio)carbonyl, (isobutylthio)carbonyl, (s-butylthio)carbonyl, (t-butyl thio)carbonyl or the like; a $C_{1-6}$ alkyl sulfinyl such as methyl sulfinyl, ethyl sulfinyl, t-butyl sulfinyl or the like; a $C_{2-6}$ alkenyl sulfinyl such as an allyl sulfinyl or the like; a $C_{2-6}$ alkynyl sulfinyl such as a propargyl sulfinyl or the like; a $C_{6-10}$ aryl sulfinyl such as a phenyl sulfinyl or the like; a heterocyclyl sulfinyl such as a thiazolyl sulfinyl, pyridyl sulfinyl or the like; a $C_{7-11}$ aralkyl sulfinyl such as a benzyl sulfinyl, phenethyl sulfinyl or the like; a $C_{1-6}$ alkyl sulfonyl such as a methyl sulfonyl, ethyl sulfonyl, t-butyl sulfonyl or the like; a $C_{2-6}$ alkenyl sulfonyl such as an allyl sulfonyl or the like; a $C_{2-6}$ alkynyl sulfonyl such as a propargyl sulfonyl or the like; a $C_{6-10}$ aryl sulfonyl such as a phenyl sulfonyl or the like; a heterocyclyl sulfonyl such as a thiazolyl sulfonyl, pyridyl sulfonyl or the like; a $C_{7-11}$ aralkyl sulfonyl such as a benzyl sulfonyl, phenethyl sulfonyl or the like; a 5-membered heteroaryl such as a pyrrolyl, furyl, thienyl group, imidazolyl, pyrazolyl, oxazolyl, isoxazolyl, thiazolyl, isothiazolyl, triazolyl, oxadiazolyl, thiadiazolyl, tetrazolyl or the like; a 6-membered heteroaryl such as a pyridyl, pyrazinyl, pyrimidinyl, pyridazinyl, triazinyl or the like; a saturated heterocyclyl such as an aziridinyl, epoxy, pyrrolidinyl, tetrahydrofuranyl, piperidyl, piperazinyl, morpholinyl or the like; a tri $C_{1-6}$ alkyl-substituted silyl such as a trimethyl silyl, triethyl silyl, t-butyl dimethyl silyl or the like; a triphenyl silyl or the like; or the like.

Examples of halogen include, but are not particularly limited to, fluorine, chlorine, bromine, iodine, and the like.

Examples of $C_{1-6}$ alkyl include, but are not particularly limited to, $C_{1-6}$ straight-chain or branched-chain alkyl, such as methyl, ethyl, n-propyl, isopropyl, n-butyl, isobutyl, sec-butyl, tert-butyl, n-pentyl, isopentyl, neopentyl, n-hexyl, and the like.

Examples of $C_{1-4}$ haloalkyl include, but are not particularly limited to, $C_{1-4}$ straight-chain or branched-chain alkyl substituted with 1 to 9, and preferably 1 to 5, halogen atoms, such as fluoromethyl, chloromethyl, bromomethyl, iodomethyl, difluoromethyl, dichloromethyl, trichloromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2,2,3,3-tetrafluoropropyl, 3,3-difluoropropyl, 2,3,3-trifluoropropyl, 3,3,3-trifluoropropyl, 2,2,3,3,3-pentafluoropropyl, heptafluoropropyl, 4,4-difluorobutyl, 4,4,4-trifluorobutyl, 3,4,4-trifluorobutyl, 3,3,4,4-tetrafluorobutyl, 3,3,4,4-pentafluorobutyl, heptafluoroisobutyl, nonafluorobutyl and the like.

Examples of aryl include, but are not particularly limited to, phenyl, 1-naphthyl, 2-naphthyl, and the like.

Examples of aryl $C_{1-6}$ alkyl include, but are not particularly limited to, fluoro(phenyl)methyl, chloro(phenyl)methyl, difluoro(phenyl)methyl, dichloro(phenyl)methyl, 1-naphtyldifluoromethyl, 2-naphtyldifluoromethyl, 1-naphtyldichloromethyl, 2-naphtyldichloromethyl and the like.

The salts of the compounds represented by Formula (I) may be any type of salts as long as they are agriculturally acceptable. Examples of the salts include inorganic acid salts, such as a hydrochloride salt, a sulfate salt, a nitrate salt, and the like; organic acid salts, such as an acetate salt, a methanesulfonic acid salt, and the like; alkali metal salts, such as a sodium salt, a potassium salt, and the like; alkaline earth metal salts, such as a magnesium salt, a calcium salt, and the like; quaternary ammonium salts, such as dimethylammonium, triethylammonium, and the like; and the like.

Symbol n represents an integer of 0 to 2.

Among compounds (I) of the present invention, a preferable compound is a compound in which R is $C_{1-6}$ alkyl and $C_{1-4}$ haloalkyl, and a more preferable compound (I) is a compound in which R is normal propyl or 2,2,2-trifluoroethyl.

Among compounds (I) of the present invention, a preferable compound is a compound in which $A^1$ is $C_{1-6}$ alkyl, another preferable compound is a compound in which $A^1$ is fluorine, chlorine, or methyl, and a more preferable compound (I) is a compound in which $A^1$ is methyl.

Among compounds (I) of the present invention, a preferable compound is a compound in which $A^2$ is halogen and $C_{1-6}$ alkyl, and a more preferable compound (I) is a compound in which $A^2$ is fluorine, chlorine or methyl.

Among compounds (I) of the present invention, a preferable compound is a compound in which $B^1$ is hydrogen or methyl.

Among compounds (I) of the present invention, a preferable compound is a compound in which $B^2$ is $C_{1-4}$ haloalkyl, or substituted or unsubstituted aryl $C_{1-4}$ haloalkyl, and a more preferable compound (I) is a compound in which $B^2$ is difluoromethyl, trifluoromethyl, chlorodifluoromethyl, pentafluoroethyl, heptafluoropropyl or difluoro(phenyl)methyl.

Among compounds (I) of the present invention, a preferable compound is a compound in which n is an integer of 0 or 1.

The term "control" encompasses killing, extermination, reduction, and elimination. For example, "controlling a mite" encompasses killing a mite, exterminating a mite, reducing a mite, and eliminating a mite. The same applies to "control agent".

Method for preparing isoxazole compound or a salt thereof:

The isoxazole compound represented by Formula (I) of the present invention can be readily prepared according to following reaction scheme 1 to scheme 3, but is not limited to these methods.

[Reaction Scheme 1]

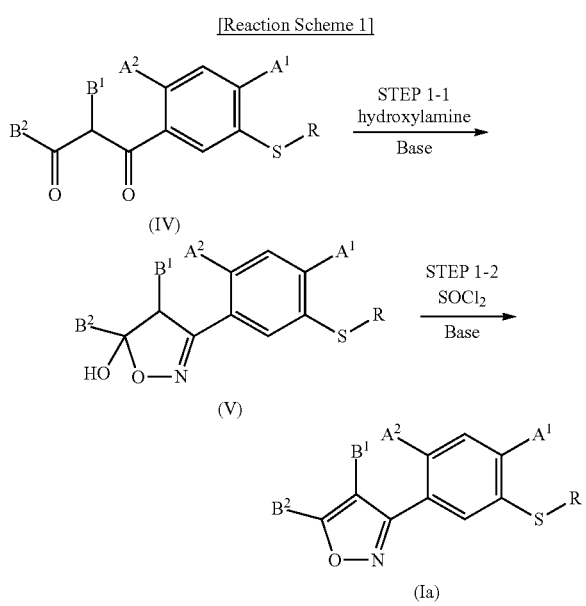

wherein R, $A^1$, $A^2$, $B^1$ and $B^2$ are as defined above.

Step 1-1

Step 1-1 is a step of preparing the compound (IV) with hydroxylamine in the presence of a base and a solvent to produce a compound (V). Depending on the type of the substituent $B^1$ and/or $B^2$, the compound (V) may not be isolated in this step and may further undergo a dehydration reaction and be converted into the compound represented by Formula (Ia) (Reaction Scheme 1-1):

[Reaction Scheme 1-1]

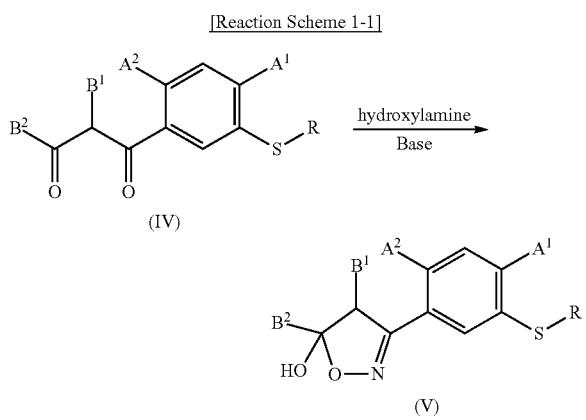

wherein R, $A^1$, $A^2$, $B^1$ and $B^2$ are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone, and the like; and sulfoxide-based solvents, such as dimethyl sulfoxide, sulfolane, and the like; $H_2O$; acetic acid, preferably methanol, ethanol and toluene. Any one of these solvents can be used alone or a combination of two or more types thereof can be used when necessary.

The amount of the solvent to be used is usually 1.0 to 20 liters, preferably 1.0 to 10 liters, per 1 mol of the compound (IV).

The aforementioned reaction can be performed under absence or presence of a base. Among the above, the reaction is performed preferably under the presence of the base. As the base, a conventionally known base can widely be used, and examples of the base include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably pyridine. Any separate one of these bases or a combination of two or more types thereof is used.

The amount of the base to be used is usually 1.0 to 5.0 mol, preferably 1.0 to 2.0 mol, per 1 mol of the compound (IV).

The hydroxylamine to be used is hydroxylamine hydrochloride, hydroxylamine sulfate or hydroxylamine hydrate, preferably hydroxylamine hydrochloride.

The amount of hydroxylamine to be used is usually 1.0 to 5.0 mol, preferably 1.0 to 2.0 mol, per 1 mol of the compound (IV).

The reaction temperature varies depending on the starting compound, the reaction reagent, the solvent and the like, but it is usually from −40° C. to the reflux temperature in the reaction system, preferably from 50 to 150° C.

The reaction time varies depending on the compound, the reaction reagent, the solvent and the reaction temperature and the like, but is usually from 10 minutes to 48 hours, preferably from 20 minutes to 24 hours, more preferably from 1 to 10 hours.

The compound (IV) used in this step can be produced according to a known method (for example, the method described in JP2008-260706A and WO2007/081019).

Step 1-2

Step 1-2 is a step of preparing the compound (V) with thionyl chloride in the presence of a base and a solvent to produce the compound represented by Formula (Ia) in which n is 0 in the compound represented by Formula (I) of the present invention (Reaction Scheme 1-2):

[Reaction Scheme 1-2]

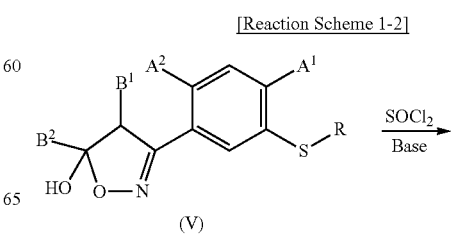

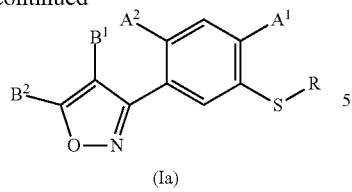

(Ia)

wherein R, $A^1$, $A^2$, $B^1$ and $B^2$ are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone and the like; and sulfoxide-based solvents, such as dimethyl sulfoxide, sulfolane and the like, preferably toluene. Any one of these solvents can be used alone or a combination of two or more types thereof can be used when necessary.

The amount of the solvent to be used is usually 0.5 to 20 liters, preferably 0.5 to 10 liters, per 1 mol of the compound (V).

The aforementioned reaction can be performed under absence or presence of a base. Among the above, the reaction is performed preferably under the presence of the base. As the base, a conventionally known base can widely be used, and examples of the base include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably pyridine. Any separate one of these bases or a combination of two or more types thereof is used.

The amount of the base to be used is usually 1.0 to 5.0 mol, preferably 1.0 to 2.0 mol, per 1 mol of the compound (V).

The amount of the thionyl chloride to be used is usually 1.0 to 6.0 mol, preferably 1.0 to 3.0 mol, per 1 mol of the compound (V).

The reaction temperature varies depending on the starting compound, the reaction reagent, the solvent and the like, but it is usually from −40° C. to the reflux temperature in the reaction system, preferably from 0 to 120° C.

The reaction time varies depending on the compound, the reagent, the solvent and the reaction temperature and the like, but is usually from 10 minutes to 48 hours, preferably from 20 minutes to 24 hours, more preferably from 1 to 10 hours.

[Reaction Scheme 2]

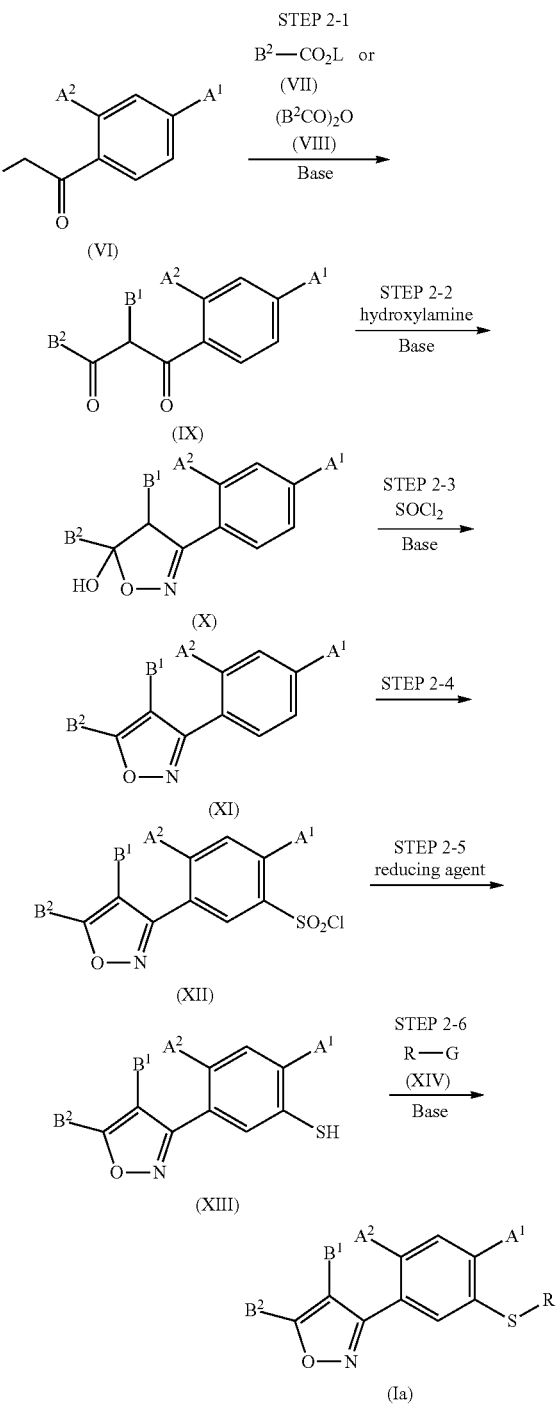

wherein R, $A^1$, $A^2$, $B^1$ and $B^2$ are as defined above.

L represents methyl or ethyl.

G represents a leaving group, and examples of the leaving groups include: halogen such as chlorine, bromine, and iodine; substituted or unsubstituted $C_{1-6}$ alkyl sulfonate; and substituted or unsubstituted aryl sulfonate. Examples of the substituents include the aforementioned substituents such as halogen and $C_{1-6}$ alkyl.

Step 2-1

Step 2-1 is a step of preparing the compound VI with compound (VII) or compound (VIII) in the presence of a base and a solvent to produce the compound (IX) (Reaction Scheme 2-1):

[Reaction Scheme 2-1]

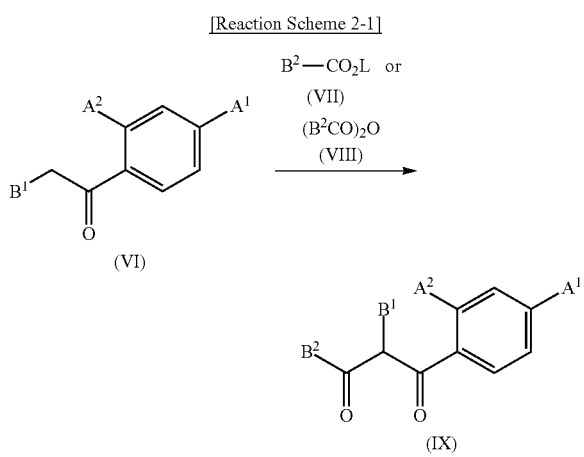

wherein R, $A^1$, $A^2$, $B^1$, $B^2$ and L are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone and the like; and sulfoxide-based solvents, such as dimethyl sulfoxide, sulfolane, and the like, preferably tetrahydrofuran and N,N-dimethylformamide. Any one of these solvents can be used alone or a combination of two or more types thereof can be used when necessary.

The amount of the solvent to be used is usually 0.5 to 20 liters, preferably 0.5 to 10 liters, per 1 mol of the compound (VI).

The aforementioned reaction can be performed under absence or presence of a base. Among the above, the reaction is performed preferably under the presence of the base. As the base, a conventionally known base can widely be used, and examples of the bases include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably pyridine, sodium hydride and sodium methoxide. Any separate one of these bases or a combination of two or more types thereof is used.

The amount of the base to be used is usually 1.0 to 5.0 mol, preferably 1.0 to 2.0 mol, per 1 mol of the compound (VI).

The amount of compound (VII) or compound (VIII) to be used is usually 1.0 to 3.0 mol, preferably 1.0 to 2.0 mol, per 1 mol of the compound (VI).

The reaction temperature varies depending on the starting compound, the reagent, the solvent and the like, but it is usually from −40° C. to the reflux temperature in the reaction system, preferably from 0 to 120° C.

The reaction time varies depending on the compound, the reagent, the solvent and the reaction temperature and the like, but is usually from 10 minutes to 48 hours, preferably from 10 minutes to 48 hours, more preferably from 20 minutes to 24 hours.

Step 2-2

Step 2-2 is a step of preparing the compound (IX) with hydroxylamine in the presence of a base and a solvent to prepare a compound (X). Depending on the type of the substituent $B^1$ and/or $B^2$, the compound (X) may not be isolated in this step and may further undergo a dehydration reaction and be converted into the compound represented by Formula (Ia) (Reaction Scheme 2-2):

[Reaction Scheme 2-2]

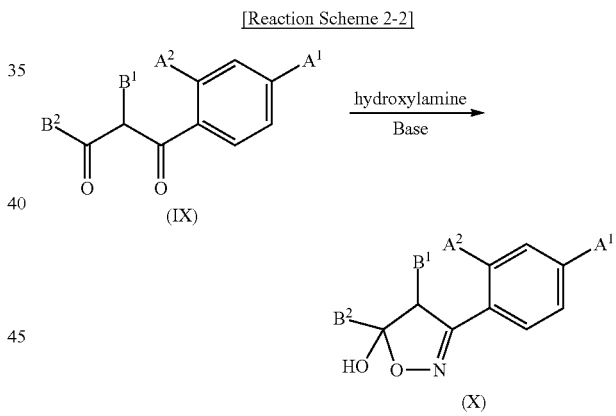

wherein R, $A^1$, $A^2$, $B^1$ and $B^2$ are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone and the like; and sulfoxide-based solvents, such as dimethyl sulfoxide, sulfolane and the like; H₂O; acetic acid, preferably methanol, ethanol and toluene. Any one of these solvents can be used alone or a combination of two or more types thereof can be used when necessary.

The amount of the solvent to be used is usually 1.0 to 20 liters, preferably 1.0 to 10 liters, per 1 mol of the compound (IX).

The aforementioned reaction can be performed under absence or presence of a base. Among the above, the reaction is performed preferably under the presence of the base. As the base, a conventionally known base can widely be used, and examples of the base include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably pyridine. Any separate one of these bases or a combination of two or more types thereof is used.

The amount of the base to be used is usually 1.0 to 5.0 mol, preferably 1.0 to 2.0 mol, per 1 mol of the compound (IX).

The hydroxylamine to be used is hydroxylamine hydrochloride, hydroxylamine sulfate or hydroxylamine hydrate, preferably hydroxylamine hydrochloride.

The amount of hydroxylamine to be used is usually 1.0 to 5.0 mol, preferably 1.0 to 2.0 mol, per 1 mol of the compound (IX).

The reaction temperature varies depending on the starting compound, the reaction reagent, the solvent and the like, but it is usually from −40° C. to the reflux temperature in the reaction system, preferably from 50 to 150° C.

The reaction time varies depending on the compound, the reaction reagent, the solvent and the reaction temperature and the like, but is usually from 10 minutes to 48 hours, preferably from 20 minutes to 24 hours, more preferably from 1 to 10 hours.

The compound (IX) used in this step can be also produced according to a known method (for example, the method described in J. Org. Chem., 55, 1959-1964(1990)).

Step 2-3

Step 2-3 is a step of preparing the compound (X) with thionyl chloride in the presence of a base and a solvent to produce the compound (XI) (Reaction Scheme 2-3):

[Reaction Scheme 2-3]

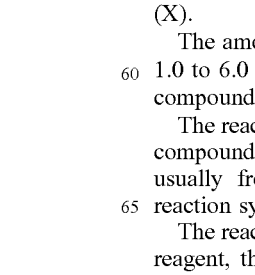

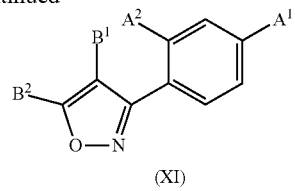

wherein A¹, A², B¹ and B² are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone and the like; and sulfoxide-based solvents, such as dimethyl sulfoxide, sulfolane and the like, preferably toluene. Any one of these solvents can be used alone or a combination of two or more types thereof can be used when necessary.

The amount of the solvent to be used is usually 0.5 to 20 liters, preferably 0.5 to 10 liters, per 1 mol of the compound (X).

The aforementioned reaction can be performed under absence or presence of a base. Among the above, the reaction is performed preferably under the presence of the base. As the base, a conventionally known base can widely be used, and examples of the base include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably pyridine. Any separate one of these bases or a combination of two or more types thereof is used.

The amount of the base to be used is usually 1.0 to 5.0 mol, preferably 1.0 to 2.0 mol, per 1 mol of the compound (X).

The amount of the thionyl chloride to be used is usually 1.0 to 6.0 mol, preferably 1.0 to 3.0 mol, per 1 mol of the compound (X).

The reaction temperature varies depending on the starting compound, the reagent, the solvent and the like, but it is usually from −40° C. to the reflux temperature in the reaction system, preferably from 0 to 120° C.

The reaction time varies depending on the compound, the reagent, the solvent and the reaction temperature and the like, but is usually from 10 minutes to 48 hours, preferably from 20 minutes to 24 hours, more preferably from 1 to 10 hours.

Step 2-4

Step 2-4 is a step of preparing the compound (XI) with chlorosulfonic acid in the absence of a solvent or in the presence of a solvent to produce the compound (XII). It can also be produced by sulfonation of the compound (XI), followed by chlorosulfonation (Reaction Scheme 2-4):

[Reaction Scheme 2-4]

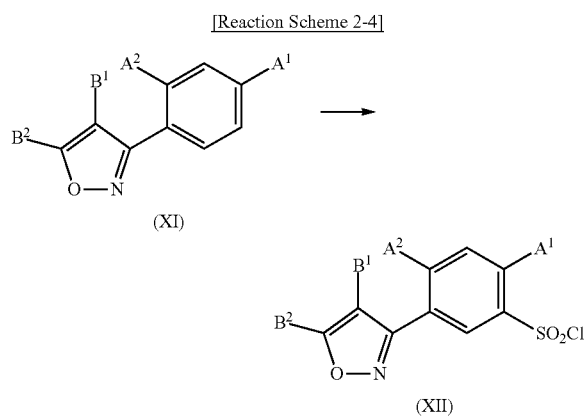

wherein $A^1$, $A^2$, $B^1$ and $B^2$ are as defined above.

A reagent used for the chlorosulfonation is not particularly limited, and for example, include chlorosulfonic acid, and the like. When using chlorosulfonic acid, the step can be carried out in one step. For the chlorosulfonation, a two-step method including sulfonation and then chlorination can be used. The compound (XII) can be produced by reacting the isoxazole compound (XI) with a sulfonation reagent to produce an HOSO2-substituted compound (XI) and then reacting the $HOSO_2$-containing compound (XI) with a chlorination agent.

The reagent used for the sulfation is not particularly limited, and for example, chlorosulfonic acid and sulfuric acid are provided. Examples of the chlorinating agent used for the chlorination include, but are not particularly limited to, chlorine, $POCl_3$, $SOCl_2$, $SO_2Cl_2$, and oxalyl chloride.

When the chlorosulfonic acid is used, a used ratio between the compound (XI) and the chlorosulfonic acid in the reaction therebetween is not particularly limited and can appropriately be selected from a wide range. The amount of the chlorosulfonic acid to be used is usually 1.0 to 50 mol, preferably 2.0 to 20 mol, per 1 mol of the compound (XI).

When the sulfonation reagent and the chlorinating agent are used, a used ratio between the sulfonation reagent and the chlorinating agent in the reaction between the compound (XI) and the sulfonation reagent is not particularly limited and can appropriately be selected from a wide range. The amount of the sulfonation reagent to be used is usually 1.0 to 50 mol, preferably 1.0 to 20 mol, per 1 mol of the compound (XI). A used ratio in the reaction between the compound (XI) and the chlorinating agent is not particularly limited, and can appropriately be selected from a wide range. The amount of the chlorinating agent to be used is usually 1.0 to 50 mol, preferably 1.0 to 20 mol, per 1 mol of the compound (XI).

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: halogenated hydrocarbon-based solvents, such as methylene chloride, 1,2-dichloroethane, chloroform, and carbon tetrachloride, and the like, preferably chloroform.

The amount of the solvent to be used is usually 1.0 to 20 liters, preferably 1.0 to 10 liters, per 1 mol of the compound (XI).

The reaction temperature varies depending on the starting compound, the reagent, the solvent and the like, but it is usually from −40° C. to the reflux temperature in the reaction system, preferably from 0 to 80° C.

The reaction time varies depending on the compound, the reagent, the solvent and the reaction temperature and the like, but is usually from 10 minutes to 48 hours, preferably from 5 minutes to 24 hours.

Step 2-5

Step 2-5 is a step of preparing the reducing agent and the compound (XII) in the presence of a solvent or absence of a solvent to produce the compound (XIII) (Reaction Scheme 2-5):

[Reaction Scheme 2-5]

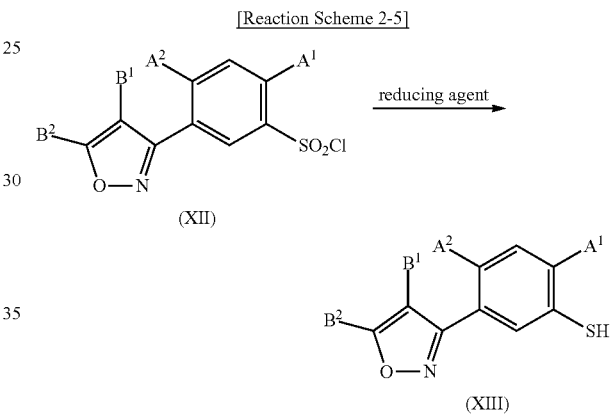

wherein $A^1$, $A^2$, $B^1$ and $B^2$ are as defined above.

The used ratio between the compound (XII) and the reducing agent in the reaction is not particularly limited and can appropriately be selected from a wide range.

As the reducing agent, any of conventionally known reducing agents can widely be used, and examples of the reducing agent include: phosphorous compounds, such as triphenylphosphine and the like; reducing agents containing metal and acid such as zinc and acid, tin (II) and acid, and iron and acid; and specific reducing agents, such as reducing agent red phosphorus, iodine, dichlorodimethylsilane-zinc-dimethylacetamide, lithium aluminum hydride, and the like. Examples of the acid include organic acids, such as acetic acid and the like; and inorganic acids, such as hydrochloric acid, sulfuric acid, and the like.

A used ratio between the compound (XII) and the reducing agent in the reaction is not particularly limited and can appropriately be selected from a wide range.

The amount of zinc and acid to be used is usually 1.0 to 50.0 mol, preferably 1.0 to 20.0 mol, per 1 mol of the compound (XII).

The aforementioned reaction is performed in an appropriate solvent. No limitations are placed on the solvent as long as the solvent is inactive with respect to the reaction. Examples of such a solvent include: $H_2O$; carboxylic acid-based solvents, such as acetic acid, propionic acid and the like; alcohols-based solvents, such as methanol, ethanol, n-propanol, isopropanol, and the like. Any one of these solvents can be used alone or a combination of two or more types thereof can be used whenever necessary, preferably H₂O and alcohols, more preferably H₂O and isopropanol.

The amount of the solvent to be used is usually 1.0 to 20 liters, preferably 1.0 to 10 liters, per 1 mol of the compound (XII).

The reaction temperature varies depending on the starting compound, the reaction reagent, the solvent and the like, but it is usually from −40° C. to the reflux temperature in the reaction system, preferably from 0 to 150° C.

The reaction time varies depending on the compound, the reagent, the solvent and the reaction temperature and the like, but is usually from 10 minutes to 48 hours, preferably from 5 minutes to 24 hours.

Step 2-6

Step 2-6 is a step of preparing the compound (XIII) with an alkyl agent (XIV) in the presence of a base and a solvent to produce a compound represented by Formula (Ia) in which n is 0 in the compound represented by Formula (I) of the present invention(Reaction Scheme 2-6):

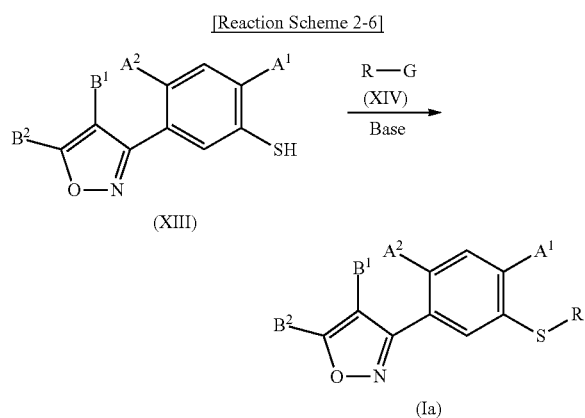

wherein R, A¹, A², B¹, B² and G are as defined above.

A used ratio between the thiol compound (XIII) and the alkyl reagent (XIV) in the reaction is not particularly limited and can appropriately be selected from a wide range. The amount of alkyl reagent (XIV) to be used is usually 1.0 to 5.0 mol, preferably 1.0 to 2.0 mol, per 1 mol of the compound (XIII).

The aforementioned reaction can be performed under absence or presence of a base. Among the above, the reaction is performed preferably under the presence of the base. As the base, a conventionally known base can widely be used, and examples of the base include: inorganic bases, such as alkali metal carbonates, such as sodium carbonate, potassium carbonate, cesium carbonate, potassium bicarbonate, sodium bicarbonate, and the like; alkali metal hydroxides, such as sodium hydroxide, potassium hydroxide, and the like; alkali metal hydrides, such as sodium hydride and potassium hydride, and the like; alkali metal alkoxides, such as sodium methoxide, sodium ethoxide, potassium tert-butoxide, and the like; organic bases, such as pyridine, triethylamine, diethylamine, dimethylamine, methylamine, imidazole, benzimidazole, diisopropylethylamine, 4-dimethylaminopyridine, piperidine, and the like; and the like, preferably alkali metal carbonates and alkali metal hydrides, more preferably sodium carbonate, potassium carbonate, potassium bicarbonate, sodium bicarbonate and sodium hydride. Any separate one of these bases or a combination of two or more types thereof is used.

The amount of the base to be used is usually 1.0 to 5.0 mol, preferably 1.0 to 3.0 mol, per 1 mol of the compound (XIII).

The aforementioned reaction can be performed by further adding a radical initiator. Examples of the radical initiator include, but are not particularly limited to, sulfurous acid, a sulfurous acid salt, Rongalite (compound name, sodium-formaldehyde-sulfoxylate), sulfurous acid adducts, and the like. The base and the radical initiator can be used in combination.

When the radical initiator is used, as an additive amount thereof, the amount of the radical initiator to be used is usually 0.1 to 10.0 mol, preferably 0.1 to 5.0 mol, per 1 mol of the compound (XIII).

The aforementioned reaction is performed in an appropriate solvent. Examples of the solvent include: fatty acid or alicyclic hydrocarbon-based solvents, such as n-hexane, cyclohexane n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, carbon tetrachloride, and the like; ether-based solvents, such as diethyl ether, THF, 1,4-dioxane, and the like; ester-based solvents, such as methyl acetate, ethyl acetate, and the like; acetonitrile; amide-based solvents, such as DMF, N,N-dimethylacetamide, N-methyl-2-pyrrolidone, and the like; sulfoxide-based solvents, such as dimethyl sulfoxide, sulfolane, and the like; polar solvents, such as alcohol-based solvents, such as methanol, ethanol, isopropyl alcohol, and the like; water; and the like. Any one of these solvents can be used alone or a combination of two or more types thereof can be used when necessary.

The amount of the solvent to be used is usually 1.0 to 20 liters, preferably 1.0 to 10 liters, per 1 mol of the compound (XIII).

The reaction temperature varies depending on the starting compound, the reagent, the solvent and the like, but it is usually from −40° C. to the reflux temperature in the reaction system, preferably from 0 to 100° C.

The reaction time varies depending on the compound, the reagent, the solvent and the reaction temperature and the like, but is usually from 5 minutes to 48 hours, preferably from 10 minutes to 24 hours.

The compound represented by Formula (Ia) obtained by the method shown in Step 2-6 is easily isolated from a reaction mixture and can be purified by use of typical isolation means and purification means, for example, filtration, solvent extraction, distillation, recrystallization, column chromatography, etc. After end of the reaction, the compound represented by Formula (Ia) can be provided for next reaction without being isolated from the reaction system.

[Reaction Scheme 3]

Step 3

Step 3 is a step of preparing the compound represented by Formula (Ia) with an oxidizing agent in the presence of a solvent to prepare a compound represented by Formula (Ib) in which n is 1 and 2 in the compound represented by Formula (I) of the present invention (Reaction Scheme 3):

[Reaction Scheme 3]

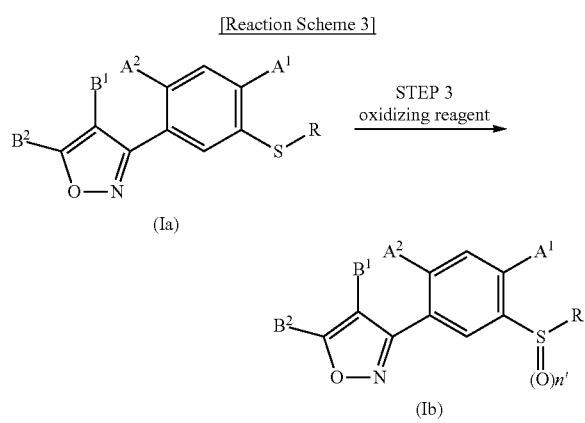

wherein n' represents an integer of 1 to 2; R, $A^1$, $A^2$, $B^1$ and $B^2$ are as defined above.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty acid or alicyclic hydrocarbon-based solvents, such as n-hexane, cyclohexane, n-heptane, and the like; aromatic hydrocarbon-based solvents, such as benzene, chlorobenzene, toluene, xylene, and the like; halogenated hydrocarbon-based solvents, such as methylene chloride, 1,2-dichloroethane, chloroform, and carbon tetrachloride, and the like; ether-based solvents, such as diethyl ether, tetrahydrofuran (THF), 1,4-dioxane, and the like; ester-based solvents, such as methyl acetate, ethyl acetate, and the like; acetonitrile; amide-based solvents, such as N,N-dimethylformamide (DMF), N,N-dimethylacetamide, N-methyl-2-pyrrolidone and the like; and ketone-based solvents, such as acetone, methyl ethyl ketone, cyclohexanone, and the like; and sulfoxide-based solvents, such as dimethyl sulfoxide, sulfolane and the like; $H_2O$; acetic acid, preferably methylene chloride, chloroform, methanol, ethanol and toluene. Any one of these solvents can be used alone or a combination of two or more types thereof can be used when necessary.

The amount of the solvent to be used is usually 0.5 to 20 liters, preferably 0.5 to 10 liters, per 1 mol of the compound represented by Formula (Ia).

The aforementioned reaction can be performed under presence of the oxidizing agent. As the oxidizing agent, any of known oxidizing agents can be used as long as the oxidizing agent can achieve the oxidization of sulfide into sulfoxide, and examples of the oxidizing agent include a combination of: peracids, such as performic acid, peracetic acid, pertrifluoroacetic acid, perbenzoic acid, m-chloroperbenzoic acid (mCPBA), o-carbonylperbenzoic acid, and the like; alkyl hydroperoxides, such as hydrogen peroxide, t-butylhydroperoxide, cumene hydroperoxide, and the like; and titanium tetraalkoxides, such as titanium tetraisopropoxide and the like; dichromate salts, such as dichromate, sodium bichromate, potassium bichromate, and the like; and permanganates, such as permanganic acid, sodium permanganate, potassium permanganate, and the like; and the like, preferably m-chloroperbenzoic acid (mCPBA) and hydrogen peroxide. Any separate one of these oxidizing agents or a combination of two or more types thereof is used.

The amount of the base to be used is usually 1.0 to 10.0 mol, preferably 1.0 to 5.0 mol, per 1 mol of the compound represented by Formula (Ia).

The aforementioned reaction can further be performed by adding a catalyst.

The reaction temperature varies depending on the starting compound, the reagent, the solvent and the like, but it is usually from −20° C. to the reflux temperature in the reaction system, preferably from −10 to 60° C.

The reaction time varies depending on the compound, the reagent, the solvent and the reaction temperature and the like, but is usually from 10 minutes to 48 hours, preferably from 20 minutes to 24 hours.

The compound represented by Formula (Ib) obtained by the method shown in Step 3 is easily isolated from a reaction mixture to be purified by use of typical isolation means and purification means, for example, filtration, solvent extraction, distillation, recrystallization, chromatography, etc.

Each compound represented by Formula (I) obtained after the completion of the reactions shown in Reaction Scheme 1 to Reaction Scheme 3 may be easily isolated from the reaction mixture and purified by known isolation and purification techniques, such as filtration, solvent extraction, distillation, recrystallization, and column chromatography.

The present mite and nematode control agent may as necessary contain an additive component (carrier) ordinarily used in agricultural chemical formulations.

The additive component can be a carrier (e.g. solid carrier or liquid carrier), a surfactant, a binder or a tackifier, a thickening agent, a coloring agent, a spreader, a sticker, an anti-freeze, a solidification inhibitor, a disintegrator, a decomposition inhibitor, etc. As necessary, other additive components such as antiseptic, vegetable chip and the like can be used. These additive components may be used in one kind or in combination of two or more kinds.

The above additive components are explained.

The solid carrier can be, for example, mineral carriers such as pyrophyllite clay, kaolin clay, silicastone clay, talc, diatomaceous earth, zeolite, bentonite, acid clay, active clay, Attapulgus clay, vermiculite, perlite, pumice, white carbon (e.g. synthetic silicic acid or synthetic silicate), titanium dioxide and the like; vegetable carriers such as wood flour, corn culm, walnut shell, fruit stone, rice hull, sawdust, wheat bran, soybean flour, powder cellulose, starch, dextrin, saccharide and the like; inorganic salt carriers such as calcium carbonate, ammonium sulfate, sodium sulfate, potassium chloride and the like; and polymer carriers such as polyethylene, polypropylene, polyvinyl chloride, polyvinyl acetate, ethylene-vinyl acetate copolymer, urea-aldehyde resin and the like.

The liquid carrier can be, for example, monohydric alcohols such as methanol, ethanol, propanol, isopropanol, butanol, cyclohexanol and the like; polyhydric alcohols such as ethylene glycol, diethylene glycol, propylene glycol, hexylene glycol, polyethylene glycol, polypropylene glycol, glycerine and the like; polyhydric alcohol derivatives such as propylene type glycol ether and the like; ketones such as acetone, methyl ethyl ketone, methyl isobutyl ketone, diisobutyl ketone, cyclohexanone, isophorone and the like; ethers such as ethyl ether, 1,4-dioxane, cellosolve, dipropyl ether, tetrahydrofuran and the like; aliphatic hydrocarbons such as normal paraffin, naphthene, isoparaffin, kerosene, mineral oil and the like; aromatic hydrocarbons such as toluene, $C_{9-10}$alkylbenzene, xylene, solvent naphtha, alkylnaphthalene, high-boiling aromatic hydrocarbon and the like; halogenated hydrocarbons such as 1,2-dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, coconut oil, castor oil and the like; and water.

As for the surfactant, there is no particular restriction. However, the surfactant preferably gels or swells in water. The surfactant can be, for example, non-ionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether-formalin condensate, polyoxyethylene polyoxypropylene block polymer, alkyl polyoxyethylene polypropylene block polymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether type silicone, ester type silicone, fluorine-containing surfactant, polyoxyethylene castor oil, polyoxyethylene hardened castor oil and the like; anionic surfactants such as alkyl sulfate, polyoxyethylene alkyl ether sulfate, polyoxyethylene alkyl phenyl ether sulfate, polyoxyethylene styryl phenyl ether sulfate, alkylbenzenesulfonic acid salt, ligninsulfonic acid salt, alkylsulfosuccinic acid salt, naphthalenesulfonic acid salt, alkylnaphthalenesulfonic acid salt, naphthalenesulfonic acid-formalin condensate salt, alkylnaphthalenesulfonic acid-formalin condensate salt, fatty acid salt, polycarboxylic acid salt, N-methyl-fatty acid sarcosinate, resin acid salt, polyoxyethylene alkyl ether phosphate, polyoxyethylene alkylphenyl ether phosphate and the like; cationic surfactants including alkyl amine salts such as laurylamine hydrochloride, stearylamine hydrochloride, oleylamine hydrochloride, stearylamine acetate, stearylaminopropylamine acetate, alkyl trimethyl ammonium chloride, alkyl dimethyl benzalkonium chloride and the like; and ampholytic surfactants such as betaine type (e.g. dialkyldiaminoethylbetaine or alkyldimethylbenzylbetaine), amino acid type (e.g. dialkylaminoethylglycine or alkyldimethylbenzylglycine) and the like.

The binder and tackifier can be, for example, carboxymethyl cellulose or a salt thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and natural phospholipid (e.g. cephalinic acid or lecithin).

The thickening agent can be, for example, water-soluble polymers such as xanthan gum, guar gum, carboxymethyl cellulose, polyvinylpyrrolidone, carboxyvinyl polymer, acrylic polymer, starch derivative, polysaccharide and the like; and inorganic fine powders such as high-purity bentonite, white carbon and the like.

The coloring agent can be, for example, inorganic pigments such as iron oxide, titanium oxide, Prussian Blue and the like; and organic dyes such as Alizarine dye, azo dye, metal phthalocyanine dye and the like.

The spreader can be, for example, silicone-based surfactant, cellulose powder, dextrin, processed starch, polyaminocarboxylic acid chelate compound, crosslinked polyvinylpyrrolidone, maleic acid and styrene, methacrylic acid copolymer, half ester between polyhydric alcohol polymer and dicarboxylic acid anhydride, and water-soluble salt of polystyrenesulfonic acid.

The sticker can be, for example, surfactant (e.g. sodium dialkylsulfosuccinate, polyoxyethylene alkyl ether, polyoxyethylene alkylphenyl ether, or polyoxyethylene fatty acid ester), paraffin, terpene, polyamide resin, polyacrylic acid salt, polyoxyethylene, wax, polyvinyl alkyl ether, alkylphenol-formalin condensate, and synthetic resin emulsion.

The anti-freeze can be, for example, polyhydric alcohol (e.g. ethylene glycol, diethylene glycol, propylene glycol, or glycerine).

The solidification inhibitor can be, for example, polysaccharide (e.g. starch, alginic acid, mannose or galactose), polyvinylpyrrolidone, white carbon, ester gum and petroleum resin.

The disintegrator can be, for example, sodium tripolyphosphate, sodium hexametaphosphate, stearic acid metal salt, cellulose powder, dextrin, methacrylic acid ester copolymer, polyvinylpyrrolidone, polyaminocarboxylic acid chelate compound, sulfonated styrene-isobutylene-maleic anhydride copolymer, and starchpolyacrylonitrile graft copolymer.

The decomposition inhibitor can be, for example, desiccants such as zeolite, quick lime, magnesium oxide and the like; antioxidants such as phenol type, amine type, sulfur type, phosphoric acid type and the like; and ultraviolet absorbents such as salicylic acid type, benzophenone type and the like.

When the present pest control agent contains the above-mentioned additive components, their contents based on mass are selected in a range of ordinarily 5 to 95%, preferably 20 to 90% in the case of carrier (e.g. solid carrier or liquid carrier), ordinarily 0.1 to 30%, preferably 0.5 to 10% in the case of surfactant, and ordinarily 0.1 to 30%, preferably 0.5 to 10% in the case of other additives.

The present pest control agent is used in any formulation selected from dust formulation, dust-granule mixture, granule, wettable powder, water-soluble concentrate, water-dispersible granule, tablet, Jumbo, emulsifiable concentrate, oil formulation, solution, flowable concentrate, emulsion, microemulsion, suspoemulsion, ultra-low volume formulation, microcapsule, smoking agent, aerosol, baiting agent, paste, etc.

In actual use of the formulation, the formulation can be used per se or after dilution with a diluent (e.g. water) in a given concentration. The application of the formulation containing the present compound or of its dilution product can be conducted by a method ordinarily used, such as dispersion (e.g. spraying, misting, atomizing, powder dispersion, granule dispersion, on-water-surface dispersion, or inbox dispersion), in-soil application (e.g. mixing or drenching), on-surface application (e.g. coating, dust coating or covering), immersion, poison bait, smoking and the like. It is also possible to mix the above-mentioned active ingredient with a livestock feed in order to prevent the infestation and growth of injurious pest, particularly injurious insect in the excreta of livestock.

The proportion (mass %) of the active ingredient in the present pest control agent is appropriately selected so as to meet the necessity. The active ingredient is appropriately selected, for example, in the following range.

In dust formulation, dust-granule mixture, etc.
0.01 to 20%, preferably 0.05 to 10%
In granule, etc.
0.1 to 30%, preferably 0.5 to 20%
In wettable powder, water-dispersible granule, etc.
1 to 70%, preferably 5 to 50%
In water-soluble concentrate, solution, etc.
1-95%, preferably 10 to 80%
In emulsifiable concentrate, etc.
5 to 90%, preferably 10 to 80%
In oil formulation, etc.
1 to 50%, preferably 5 to 30%
In flowable concentrate, etc.
5 to 60%, preferably 10 to 50%
In emulsion, microemulsion, suspoemulsion, etc.
5 to 70%, preferably 10 to 60%
In tablet, bait, paste, etc.
1 to 80%, preferably 5 to 50%
In smoking agent, etc.
0.1 to 50%, preferably 1 to 30%
In aerosol, etc.
0.05 to 20%, preferably 0.1 to 10%

The formulation is sprayed after dilution in an appropriate concentration, or applied directly.

When the present pest control agent is used after dilution with a diluent, the concentration of active ingredient is generally 0.1 to 5,000 ppm. When the formulation is used per se, the application amount thereof per unit area is 0.1 to 5,000 g per 1 ha in terms of active ingredient compound; however, the application amount is not restricted thereto.

Incidentally, the present pest control agent is sufficiently effective when using the present compound alone as an active ingredient. However, the present pest control agent may be mixed or used in combination, as necessary, with fertilizers and agricultural chemicals such as insecticide, miticide, nematocide, synergist, fungicide, antiviral agent, attractant, herbicide, plant growth-controlling agent and the like. In this case, a higher effect is exhibited.

Below are examples of the known insecticides, miticides, nematocides and synergist compounds, which may be mixed or used in combination.

1. Acetylcholine Esterase Inhibitors (1A) carbamates: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC (vamidothion), xylylcarb;

(1B) Organophosphates: acephate, azamethiphos, azinphosethyl, azinphos-methyl, cadusafos, chlorethoxyfos, chlorfenvinphos, chlormephos, chlorpyrifos, chlorpyrifosmethyl, coumaphos, cyanophos, demeton-S-methyl, diamidafos, diazinon, dichlorvos, dicrotophos, dimethoate, dimethylvinphos, dioxabenzofos, disulfoton, DSP (O,O-diethyl O-(4-dimethyl sulfamoylphenyl)phosphorothioate), EPN (O-ethyl O-4-nitrophenyl phenylphosphonothioate), ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-(methoxyaminothio-phosphoryl)salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos, flupyrazofos 2. GABA-Gated Chloride Channel Antagonists (2A) Cyclodiene organochlorines: chlordane, endosulfan, gamma-BHC (benzene hexachloride);

(2B) Phenylpyrazoles: acetoprole, ethiprole, fipronil, pyrafluprole, pyriprole, RZI-02-003 (code number) 3. Sodium channel modulators (3A) Pyrethroids/Pyrethrins: acrinathrin, allethrin (includes d-cis-trans and d-trans), bifenthrin, bioallethrin, bioallethrin S-cyclopentenyl, bioresmethrin, cycloprothrin, cyfluthrin (includes beta-), cyhalothrin (includes gamma- and lambda-), cypermethrin (includes alpha-, beta-, theta- and zeta-), cyphenothrin [includes (IR)-trans-isomers], deltamethrin, empenthrin, esfenvalerate, etofenprox, fenpropathrin, fenvalerate, flucythrinate, flumethrin, halfenprox, imiprothrin, metofluthrin, permethrin, phenothrin [includes (IR)-trans-isomer], prallethrin, profluthrin, pyrethrine, resmethrin, RU15525 (code number), silafluofen, tefluthrin, tetramethrin, tralomethrin, transfluthrin, ZX18901 (code number), fluvalinate (includes tau-), tetramethylfluthrin, meperfluthrin;

(3B) DDT/Methoxychlor: DDT (1,1,1-trichloro-2,2-bis (4-chlorophenyl)ethane), methoxychlor 3. Nicotinic Acetylcholine Receptor Agonist/Antagonist (4A) Neonicotinoids: acetamiprid, clothianidin, dinotefuran, imidacloprid, nitenpyram, thiacloprid, thiamethoxam;

(4B) Nicotine: nicotine-sulfate

4. Nicotinic Acetylcholine Receptor Allosteric Ctivators

Spinosines: spinetoram, spinosad

5. Chloride Channel Activators

Abamectins, Milbemycins: abamectin, emamectin benzoate, lepimectin, milbemectin, ivermectin, polynactins 6. Juvenile Hormone Mimics diofenolan, hydroprene, kinoprene, methothrin, fenoxycarb, pyriproxyfen 7. Miscellaneous Non-Specific (Multi-Site) Inhibitors 1,3-dichloropropene, DCIP (bis(2-chloro-1-methylethyl) ether), ethylene dibromide, methyl bromide, chloropicrin, sulfuryl fluoride 8. Antifeedant pymetrozine, flonicamid, pyrifluquinazon 9. Mite Growth Inhibitor clofentezine, diflovidazin, hexythiazox, etoxazole 10. Microbial Disruptors of Insect Midgut Membranes BT (*Bacillus thuringiensis*) agent: *Bacillus sphaericus, Bacillus thuringiensis* subsp. *aizawai, Bacillus thuringiensis* subsp. *israelensis, Bacillus thuringiensis* subsp. *kurstaki, Bacillus thuringiensis* subsp. *tenebrionis,* Bt crop proteins (Cry1Ab, Cry1Ac, Cry1Fa, Cry2Ab, mCry3A, Cry3Ab, Cry3Bb, Cry34/35Ab1), *Bacillus popilliae, Bacillus subtillis*

11. Inhibitors of Mitochondrial ATP Synthase diafenthiuron; Organotin miticides: azocyclotin, cyhexatin, fenbutatin oxide; propargite, tetradifon 12. Uncouplers of Oxidative Phosphorylation via Disruption of the Proton Gradient chlorfenapyr, DNOC (6-Methyl-2,4-dinitrophenol)

13. Nicotinic Acetylcholine Receptor Channel Blockers

Nereistoxin analogues: bensultap, cartap, thiocyclam, thiosultap

14. Inhibitors of Chitin Biosynthesis, Type O
   Benzoylureas: bistrifluron, chlorfluazoron, diflubenzuron, flucycloxuron, flufenoxuron, hexaflumuron, lufenuron, novaluron, noviflumuron, teflubenzuron, triflumuron, fluazuron
15. Inhibitors of Chitin Biosynthesis, Type 1
   buprofezin
16. Molting Disruptor, Dipteran
   cyromazine
17. Ecdysone Receptor Agonist (Ecdysis Acceleration)
   Diacylhydrazines: chromafenozide, halofenozide, methoxyfenozide, tebufenozide
18. Octopamine Receptor Agonist
   amitraz
19. Mitochondrial Complex III Electron Transport Inhibitors
   hydramethylnon, acequinocyl, fluacrypyrim, cyenopyrafen
20. Mitochondrial Complex II Electron Transport Inhibitors
   cyflumetofen, cyenopyrafen, NNI-0711 (code number)
21. Mitochondrial Complex I Electron Transport Inhibitors (METI)
   METI miticides and insecticides: fenazaquin, fenpyroximate, pyridaben, pyrimidifen, tebufenpyrad, tolfenpyrad
   Other: rotenone
22. Sodium Channel Blockers
   indoxacarb, metaflumizon
23. Inhibitors of Lipid Synthesis
   Tetronic and Tetramic acid derivatives: spirodiclofen, spiromesifen, spirotetramat
24. Mitochondrial Complex IV Electron Transport Inhibitors
   aluminum phosphide, phosphine, zinc phosphide, calcium cyanide
25. Neuronal Inhibitors (Unknown Mode of Action)
   bifenazate
26. Aconitase Inhibitors
   sodium fluoroacetate
27. Synergists
   piperonyl butoxide, DEF (phosphorotrithioic acid S,S,S-tributyl ester)
28. Ryanodine Receptor Modulators
   chlorantraniliprole, flubendiamide, cyantraniliprole
29. Compounds with Unknown Mode of Action
   azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, flsulfamide, karanjin, metham, methoprene, methoxyfenozide, methyl isothiocyanate, pyridalyl, pyrifluquinazon, sulcofuron-sodium, sulfluramid, sulfoxaflor, flupyradifurone, flometoquin, IKI-3106 (code number)
30. Entomopathogenic Fungi, Nematode-Pathogenic Microorganisms
   *Beauveria bassiana, Beauveria tenella, Verticillium lecanii, Pacilimyces tenuipes, Paecilomyces fumosoroceus, Beauveria brongniartii, Monacrosporium phymatophagum, Pasteuriapenetrans*
32. Sex Pheromone
   (Z)-11-hexadecenal, (Z)-11-hexadecenyl acetate, litlure-A, litlure-B, Z-13-eicosene-10-one, (Z,E)-9,12-tetradecadienyl acetate, (Z)-9-tetradecen-1-ol, (Z)-11-tetradecenyl acetate, (Z)-9,12-tetradecadienyl acetate, (Z,E)-9,11-detradecadienyl acetate Next, below are examples of the known fungicide or disease damage control agent compounds which may be mixed or used in combination.

1. Nucleic Acid Biosynthesis Inhibitor
   Acylalanines: benalaxyl, benalaxyl-M, furalaxyl, metalaxyl, metalaxyl-M;
   Oxazolidinones: oxadixyl;
   Butyrolactones: clozylacon, ofurace;
   Hydroxy-(2-amino)pyrimidines: bupirimate, dimethirimol, ethirimol;
   Isoxazole: hymexazol;
   Isothiazolones: octhilinone;
   Carboxylic acids: oxolinic acid
2. Mitosis and Cell Division Inhibitors
   Benzoimidazoles: benomyl, carbendazim, fuberidazole, thiabendazole;
   Thiophanates: thiophanate, thiophanate-methyl;
   N-phenylcarbamates: diethofencarb;
   Toluamides: zoxamide;
   Phenylureas: pencycuron;
   Pyridinylmethylbenzamides: fluopicolide
3. Respiratory Inhibitors
   Pyrimidineamines: diflumetorim;
   Carboxamides: benodanil, flutolanil, mepronil, fluopyram, fenfuram, carboxin, oxycarboxin, thifluzamide, bixafen, furametpyr, isopyrazam, penflufen, penthiopyrad, sedaxane, boscalid, fluxapyroxad, isofetamid, benzovindiflupyr;
   Methoxy-acrylates: azoxystrobin, enestroburin, picoxystrobin, pyraoxystrobin, coumoxystrobin, enoxastrobin, flufenoxystrobin;
   Methoxy-carbamates: pyraclostrobin, pyrametostrobin, triclopyricarb;
   Oxyimino acetates: kresoxim-methyl, trifloxystrobin;
   Oxyimino-acetamides: dimoxystrobin, metominostrobin, orysastrobin, fenaminstrobin;
   Oxazolidine-diones: famoxadone;
   Dihydro-dioxazines: fluoxastrobin;
   Imidazolinones: fenamidone;
   Benzyl-carbamates: pyribencarb;
   Cyano-imidazoles: cyazofamid;
   Sulfamoyl-triazoles: amisulbrom;
   Dinitrophenyl crotonates: binapacryl, methyldinocap, dinocap;
   2,6-Dinitro-anilines: fluazinam;
   Pyrimidinone hydrazones: ferimzone;
   Triphenyl tin: TPTA, TPTC, TPTH;
   Thiophene-carboxamides: silthiofam
   Triazolo-pyrimidylamines: ametoctradin
4. Amino Acid and Protein Synthesis Inhibitors
   Anilino-pyrimidines: cyprodinil, mepanipyrim, pyrimethanil;
   Enopyranuronic acid: blasticidin-S, mildiomycin;
   Hexopyranosyl antibiotic: kasugamycin;
   Glucopyranosyl antibiotic: streptomycin;
   Tetracycline antibiotic: oxytetracycline
5. Signal Transduction Inhibitors
   Quinoline: quinoxyfen;
   Quinazolines: proquinazid;
   Phenylpyrroles: fenpiclonil, fludioxonil;
   Dicarboxyimides: chlozolinate, iprodione, procymidone, vinclozolin
6. Lipid Synthesis and Membrane Integrity Inhibitors
   Phosphoro-thiolates: edifenphos, iprobenfos, pyrazophos;
   Dithiolanes: isoprothiolane;
   Aromatic hydrocarbons: biphenyl, chloroneb, dicloran, quintozene, tecnazene, tolclofos-methyl;
   1,2,4-Thiadiazoles: etridiazole;
   Carbamates: iodocarb, propamocarb-hydrochloride, prothiocarb;
   Cinnamic acid amides: dimethomorph, flumorph;

Valineamide carbamates: benthiavalicarb-isopropyl, iprovalicarb, valifenalate;
Mandelic acid amides: mandipropamid;
*Bacillus subtilis* and the fungicidal lipopeptides produced: *Bacillus subtilis* (strain: QST 713)
7. Inhibitors of Sterol Biosynthesis in Membranes
Piperazines: triforine;
Pyridines: pyrifenox;
Pyrimidines: fenarimol, nuarimol;
Imidazoles: imazalil, oxpoconazole-fumarate, pefurazoate, prochloraz, triflumizole;
Triazoles: azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, furconazole, furconazole-cis, quinconazole;
Morpholines: aldimorph, dodemorph, fenpropimorph, tridemorph;
Piperidines: fenpropidin, piperalin;
Spiroketal amines: spiroxamine;
Hydroxyanilides: fenhexamid;
Thiocarbamates: pyributicarb;
Allylamines: naftifine, terbinafine
8. Glucan Synthesis Inhibitors
Glucopyranosyl type antibiotic: validamycin;
Peptidylpyridine nucleotide compound: polyoxin
9. Melanine Synthesis Inhibitors
Isobenzo-furanones: phthalide;
Pyrrolo-quinolines: pyroquilon;
Triazolobenzo-thiazoles: tricyclazole;
Carboxamides: carpropamid, diclocymet;
Propionamides: fenoxanil
10. Host Plant Defence Inducers
Benzothiadiazoles: acibenzolar-S-methyl;
Benzoisothiazoles: probenazole;
Thiadiazole-carboxamides: tiadinil, isotianil
Natural product: laminarin
11. Compounds with Unknown Mode of Action
Copper compound: copper hydroxide, copper dioctanoate, copper oxychloride, copper sulfate, cuprous oxide, oxine-copper, Bordeaux mixture, copper nonyl phenol sulphonate;
Sulfur compound: sulfur;
Dithiocarbamates: ferbam, mancozeb, maneb, metiram, propineb, thiram, zineb, ziram, cufraneb;
Phthalimides: captan, folpet, captafol;
Chloronitriles: chlorothalonil;
Sulfamides: dichlofluanid, tolylfluanid;
Guanidines: guazatine, iminoctadine-albesilate, iminoctadine-triacetate, dodine;
Other compound: anilazine, dithianon, cymoxanil, fosetyl (aluminum, calcium, sodium), phosphorus acid and salts, tecloftalam, triazoxide, flusulfamide, diclomezine, methasulfocarb, ethaboxam, cyflufenamid, metrafenone, potassium bicarbonate, sodium bicarbonate, BAF-045 (code number) (5,7-dimethoxy-2-(2,4,6-trichlorophenyl)-[1,2,4]triazolo[1,5-a]pyrimidine), BAG-010 (code number), benthiazole, bronopol, carvone, chinomethionat, dazomet, DBEDC, debacarb, dichlorophen, difenzoquat-methyl sulfate, dimethyl disulfide, diphenylamine, ethoxyquin, flumetover, fluoroimide, flutianil, furancarboxylic acid, metam, nabam, natamycin, nitrapyrin, nitrothal-isopropyl, o-phenylphenol, oxazinylazole, oxyquinoline sulfate, phenazine oxide, polycarbamate, pyrofenone, fenpyrazamine, silver, pyrisoxazole, tebufloquin, tolnifanide, trichlamide, mineral oils, organic oils, tolprocarb, oxathiapiprolin Below are shown examples of the known herbicidal compounds and plant growth regulators which may be mixed or used in combination.
A1. Acetyl CoA Carboxylase (ACCase) Inhibitors
(A1-1) Aryloxyphenoxy propionates: clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-etotyl, haloxyfop-P, metamifop, propaquizafop, quizalofop-ethyl, quizalofop-P-ethyl, quizalofop-P-tefuryl, fenthiaprop-ethyl;
(A1-2) Cyclohexandiones: alloxydim, butroxydim, clethodim, cycloxydim, profoxydim, sethoxydim, tepraloxydim, tralkoxydim;
(A1-3) Phenylpyrazolines: aminopyralid, pinoxaden;
B. Acetolactate Synthase (ALS) Inhibitors
(B-1) Imidazolinones: imazamethabenz-methyl, imazamox, imazapic (includes salts with amine, etc.), imazapyr (includes salts with isopropylamine, etc.), imazaquin, imazathapyr;
(B-2) Pyrimidinyloxy benzoate: bispyribac-sodium, pyribenzoxim, pyriftalid, pyriminobac-methyl, pyrithiobac-sodium, pyrimisulfan, triafamone;
(B-3) Sulfonylaminocarbonyl-triazolinones: flucarbazone-sodium, thiencarbazone (includes sodium salt, methyl ester, etc.), propoxycarbazone-sodium, procarbazone-sodium, iofensulfuron-sodium;
(B-4) Sulfonylureas: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, thifensulfuron-methyl, triasulfuron, tribenuron-methyl, trifloxysulfuron-sodium, triflusulfuron-methyl, tritosulfuron, orthosulfamuron, propgirisulfuron, metazosulfuron, flucetosulfuron;
(B-5) Triazolopyrimidines: cloransulam-methyl, diclosulam, florasulam, flumetsulam, metosulam, penoxsulam, pyroxsulam; C1. Photosynthesis at photosystem II inhibitors (1)
($C_{1-1}$) Phenylcarbamates: desmedipham, phenmedipham;
($C_{1-2}$) Pyridazinones: chloridazon, brompyrazon;
($C_{1-3}$) Triazines: ametryn, atrazine, cyanazine, desmetryne, dimethametryn, eglinazine-ethyl, prometon, prometryn, propazine, simazine, simetryn, terbumeton, terbuthylazine, terbutryn, trietazine;
($C_{1-4}$) Triazinones: metamitron, metribuzin;
($C_{1-5}$) Triazolinones: amicarbazone;
($C_{1-6}$) Uracils: bromacil, lenacil, terbacil;
C2. Photosynthesis at Photosystem II Inhibitors (2)
($C_{2-1}$) Amides: pentanochlor, propanil;
($C_{2-2}$) Ureas: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, metobenzuron;
C3. Photosynthesis at Photosystem II Inhibitors (3)
(C3-1) Benzothiadiazones: bentazone;
(C3-2) Nitriles: bromofenoxim, bromoxynil (includes esters of butyric acid, octanoic acid, heptanoic acid, etc.), ioxynil; (C3-3) Phenylpyrazines: pyridafol, pyridate;
D. Photosystem-I-Electron Acceptors
(D-1) Bipyridyliums: diquat, paraquat dichloride;

E. Protoporphyrinogen Oxydaze (PPO) Inhibitors
(E-1) Diphenyl ethers: acifluorfen-sodium, bifenox, chlomethoxyfen, ethoxyfen-ethyl, fluoroglycofen-ethyl, fomesafen, lactofen, oxyfluorfen;
(E-2) N-phenylphthalimides: cinidon-ethyl, flumiclorac-pentyl, flumioxazin, chlorphthalim;
(E-3) Oxydiazoles: oxadiargyl, oxadiazon;
(E-4) Oxazolidinediones: pentoxazone;
(E-5) Phenylpyrazoles: fluazolate, pyraflufen-ethyl;
(E-6) Pyrimidinediones: benzfendizone, butafenacil, saflufenacil, tiafenacil;
(E-7) Thiadiazoles: fluthiacet-methyl, thidiazimin;
(E-8) Triazolinones: azafenidin, carfentrazone-ethyl, sulfentrazone, bencarbazone;
(E-9) Other compound: flufenpyr-ethyl, profluazol, pyraclonil, SYP-298 (code number), SYP-300 (code number);
F1. Inhibitors of Carotenoid Biosynthesis at the Phytoene Desaturase Step (PDS)
(F1-1) Pyridazinones: norflurazon;
(F1-2) Pyrimidinecarboxamides: diflufenican, picolinafen;
(F1-3) Other compound: beflubutamid, fluridone, flurochloridone, flurtamone;
F2. 4-Hydroxyphenyl-pyruvate-dioxygenase (HPPD) Inhibitors (F2-1) Callistemones: mesotrione;
(F2-2) Isoxazoles: pyrasulfotole, isoxaflutole, isoxachlortole;
(F2-3) Pyrazoles: benzofenap, pyrazolynate, pyrazoxyfen, topramezone;
(F2-4) Triketones: sulcotrione, tefuryltrione, tembotrione, pyrasulfotole, topramezone, bicyclopyrone;
F3. Carotinoid Biosynthesis Inhibitors (Unknown Target)
(F3-1) Diphenyl ethers: aclonifen;
(F3-2) Isoxazolidinones: clomazone;
(F3-3) Triazoles: amitrole;
G. EPSP Synthase Inhibitors (Aromatic Amino Acid Biosynthesis Inhibitors)
(G-1) Glycines: glyphosate (includes salts of sodium, amine, propylamine, ispropylamine, dimethylamine, trimesium, etc.);
H. Glutamine Synthetase Inhibitors
(H-1) Phosphinic acids: bilanafos, glufosinate (includes salts of amine, sodium, etc.);
I. Dihydropteroate (DHP) Synthetase Inhibitors
(I-1) Carbamates: asulam;
K1. Microtubule Assembly Inhibitors
(K1-1) Benzamides: propyzamide, tebutam;
(K1-2) Benzoic acids: chlorthal-dimethyl;
(K1-3) Dinitroanilines: benfluralin, butralin, dinitramine, ethalfluralin, fluchloralin, oryzalin, pendimethalin, prodiamine, trifluralin;
(K1-4) Phosphoroamidates: amiprofos-methyl, butamifos;
(K1-5) Pyridines: dithiopyr, thiazopyr;
K2. Inhibitors of Mitosis/Microtubule Organization
(K2-1) Carbamates: carbetamide, chlorpropham, propham, swep, karbutilate;
K3. Very-Long-Chain Fatty Acids (VLCFAs) Inhibitors (Cell Division Inhibitors)
(K3-1) Acetamides: diphenamid, napropamide, naproanilide;
(K3-2) Chloroacetamides: acetochlor, alachlor, butachlor, butenachlor, diethatyl-ethyl, dimethachlor, dimethenamid, dimethenamid-P, metazachlor, metolachlor, pethoxamid, pretilachlor, propachlor, propisochlor, S-metolachlor, thenylchlor;
(K3-3) Oxyacetamides: flufenacet, mefenacet;
(K3-4) Tetrazolinones: fentrazamide;
(K3-5) Other compound: anilofos, bromobutide, cafenstrole, indanofan, piperophos, fenoxasulfone, pyroxasulfone, ipfencarbazone;
L. Cellulose Synthesis Inhibitors
(L-1) Benzamides: isoxaben;
(L-2) Nitriles: dichlobenil, chlorthiamid;
(L-3) Triazolocarboxamides: flupoxame;
M. Uncouplers (Membrane Disruptors)
(M-1) Dinitrophenols: dinoterb, DNOC (includes salts of amine, sodium, etc.);
N. Lipid Biosynthesis Inhibitors (Excluding ACCase Inhibitors)
(N-1) Benzofurans: benfuresate, ethofumesate; (N-2) Halogenated carboxylic acids: dalapon, flupropanate, TCA (trichloroacetic acid) (includes salts of sodium, calcium, ammonia, etc.);
(N-3) Phosphorodithioates: bensulide;
(N-4) Thiocarbamates: butylate, cycloate, dimepiperate, EPTC, esprocarb, molinate, orbencarb, pebulate, prosulfocarb, thiobencarb, tiocarbazil, tri-allate, vernolate;
O. Synthetic auxins
(O-1) Benzoic acids: chloramben, 2,3,6-TBA (2,3,6-trichlorobenzoic acid), dicamba (includes salts of amine, diethylamine, isopropylamine, diglycolamine, sodium, lithium, etc.);
(O-2) Phenoxycarboxylic acids: 2,4,5-T, 2,4-D (includes salts of amine, diethylamine, triethanolamine, isopropylamine, sodium, lithium, etc.), 2,4-DB (4-(2,4-dichlorophenoxy)butyric acid), clomeprop, dichlorprop, dichlorprop-P, MCPA ((4-chloro-2-methylphenoxy)acetic acid), MCPA-thioethyl, MCPB (4-(4-chloro-2-methylphenoxy) butyric acid) (includes sodium salt, ethylester, etc.), mecoprop (includes salts of sodium, potassium, isopropylamine, triethanolamine, dimethylamine, etc.), mecoprop-P;
(O-3) Pyridine carboxylic acids: clopyralid, fluroxypyr, picloram, triclopyr, triclopyr-butotyl, halauxifen-methyl;
(O-4) Quinoline carboxylic acids: quinclorac, quinmerac;
(O-5) Other compound: benazolin;
P. Auxin Transport Inhibitors
(P-1) Phthalamates: naptalam (includes salts with sodium, etc.);
(P-2) Semicarbazones: diflufenzopyr;
Z. Compounds with Unknown Mode of Action
flamprop-M (includes methyl, ethyl and isopropyl esters), flamprop (includes methyl, ethyl and isopropyl esters), chlorflurenol-methyl, cinmethylin, cumyluron, daimuron, methyldymuron, difenzoquat, etobenzanid, fosamine, pyributicarb, oxaziclomefone, acrolein, AE-F-150954 (code number), aminocyclopyrachlor, cyanamide, heptamaloxyloglucan, indaziflam, triaziflam, quinoclamine, endothal-disodium, phenisopham, SL-573 (code number) (1-cyclopropylmethyl-6-methoxy-4-phenyl-2(1H)-quinazolinone),
cyclopyrimonate Plant growth-controlling agent: 1-methylcyclopropene, 1-naphthylacetamide, 2,6-diisopropylnaphthalene, 4-CPA ((4-chlorophenoxy)acetic acid), benzylaminopurine, ancymidol, aviglycine, carvone, chlormequat, cloprop, cloxyfonac, cloxyfonac-potassium, cyclanilide, cytokinins, daminozide, dikegulac, dimethipin, ethephon, ethychlozate, flumetralin, flurenol, flurprimidol, forchlorfenuron, gibberellin acid, inabenfide, indole acetic acid, indole butyric acid, maleic hydrazide, mefluidide, mepiquat chloride, n-decanol, paclobutrazol, prohexadione-calcium, prohydrojasmon, sintofen, thidiazuron, triacontanol, trinexapac-ethyl, uniconazole, uniconazole-P, 4-oxo-4-(2-phenylethyl)aminobutyric acid (chemical name, CAS registration No.: 1083-55-2)

Next, below are examples of the known safeners which may be mixed or used in combination.

benoxacor, furilazole, dichlormid, dicyclonone, DKA-24 (N1,N2-diallyl-N2-dichloroacetylglycineamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine), cloquintcet-methyl, 1,8-Naphthalic anhydride, mefenpyrdiethyl, mefenpyr, mefenpyr-ethyl, fenchlorazole 0 ethyl, fenclorim, MG-191 (2-dichloromethyl-2-methyl-1, 3-dioxane), cyometrinil, flurazole, fluxofenim, isoxadifen, isoxadifen-ethyl, mecoprop, MCPA, daimuron, 2,4-D ((2,4-dichlorophenoxy)acetic acid), MON 4660 (code number) (4-(dichloroacetyl)-1-oxa-4-azaspiro[4.5]decane), oxabetrinil, cyprosulfamide, lower alkyl-substituted benzoic acid, TI-35 (code number) and N-(2-methoxybenzoyl)-4-[(methylaminocarbonyl)amino]benzenesulfonamide(chemical name, CAS registration No.: 129531-12-0)

The pest control agent of the present invention constituted as above exhibits an excellent control effect to pest of Orthoptera, Thysanoptera, Hemiptera, Coleoptera, Diptera, Lepidoptera, Hymenoptera, Collembola, Thysanura, Blattodea, Isoptera, Psocoptera, Mallophaga, Anoplura, plant-feeding mites, plant parasitic nematodes, plant parasitic mollusc pests, other crop pests, nuisance pests, sanitary insects, parasites, etc. The following organism species are examples of such pests.

Orthopteran pest can be, for example,
Tettigoniidae: *Ruspolia lineosa*, etc.,
Gryllidae: *Teleogryllus emma*, etc.,
Gryllotalpidae: *Gryllotalpa orientalis*,
Acrididae: *Oxya hyla intricate, Locusta migratoria, Melanoplus sanguinipes*, etc.,
Pyrgomorphidae: *Atractomorpha lata*,
Eneopteridae: *Euscrytus japonicus*,
Tridactylidae: *Xya japonicus*, etc.

Thysanopteran pests can be, for example,
Thripidae: *Frankliniella intonsa, Frankliniella occidentalis, Scirtothrips dorsalis, Thrips palmi, Thrips tabaci*, etc.,
Phlaeothripidaes: Ponticulothrips diospyrosi, Haplothrips aculeatus, etc.

Hemipteran pests can be, for example,
Cicadidae: *Mogannia minuta*, etc.,
Aphrophoridae: *Aphorphora intermedia*, etc.,
Membracicdae: *Machaerotypus sibiricus*, etc.,
Cicadellidae: *Arboridia apicalis, Empoasca onukii, Nephotettix cincticeps, Recilia dorsalis*, etc.,
Cixiidae: *Pentastiridius apicalis*, etc.,
Delphacidae: *Laodelphax striatella, Nilaparvata lugens, Sogatella furcifera*, etc.,
Meenoplidae: *Nisia nervosa*, etc.,
Derbidae: *Kamendaka saccharivora*, etc.,
Cixidia okunii: *Achilus flammeus*, etc.,
Ricaniidae: *Orosanga japonicus*, etc.,
Flatidae: *Mimophantia maritima*, etc.,
Psyllidae: *Cacopsylla pyrisuga*, etc.,
Calophyidae: *Calophya mangiferae*, etc.,
Phylloxeridae: *Daktulosphaira vitifoliae*, etc.,
Adelgidae: *Adelges laricis, Adelges tsugae*, etc.,
Aphydidae: *Acyrthosiphon pisum, Aphis gossypii, Aphis spiraecola, Lipaphis erysimi, Myzus persicae, Schizaphis graminum, Rhopalosiphum padi*, etc.,
Aleyrodidae: *Aleurocanthus spiniferus, Bemisia tabaci, Bemisia argentifolii, Trialeurodes vaporariorum*, etc.,
Margarodidae: *Drosicha corpulenta, Icerya purchasi*, etc.,
Pseudococcidae: *Dysmicoccus brevipes, Planococcus citri, Pseudococcus comstocki*, etc.,
Coccidae: *Ceroplastes ceriferus*, etc.,
Aclerdidae: *Aclerda takahasii*, etc.,
Diaspididae: *Aonidella aurantii, Diaspidiotus perniciosus, Unaspis yanonensis*, etc.,
Miridae: *Lygus hesperus, Trigonotylus caelestialium*, etc.,
Tingidae: *Stephanitis pyrioides, Stephanitis nashi*, etc.,
Pentatomidae: *Eysarcoris aeneus, Lagynotomus elongatus, Nezara viridula, Plautia crossota*, etc.,
Plataspidae: *Megacopta cribaria*, etc.,
Lygaeidae: *Cavelerius saccharivorus*, etc.,
Malcidae: *Malcus japonicus*, etc.,
Pyrrhocoridae: *Dysdercus cingulatus*, etc.,
Alydidae: *Leptocorisa acuta, Leptocorisa chinensis*, etc.,
Coreidae: *Anacanthocoris striicornis*, etc.,
Rhopalidae: *Rhopalus maculatus*, etc.,
Cimicidae: *Cimex lectularis*, etc.

Coleoptera pests can be, for example,
Scarabaeidae: *Anomara cuprea, Anomara rufocuprea, Popillia japonica, Oryctes rhinoceros*, etc.,
Elateridae: *Agriotes ogurae, Melanotus okinawensis, Melanotus fortnumi fortnumi*, etc.,
Dermestidae: *Anthrenus verbasci*, etc.,
Bostrychidae: *Heterobostrychus hamatipennis*, etc.,
Anobiidae: *Stegobium paniceum*, etc.,
Ptinidae: *Pitinus clavipes*, etc.,
Trogossitidae: *Tenebroides manritanicus*, etc.,
Cleridae: *Necrobia rufipes*,
Nitidulidae: *Carpophilus hemipterus*, etc.,
Silvanidae: *Ahasverus advena*, etc.,
Laemophloeidae: *Cryptolestes ferrugineus*, etc.,
Coccinellidae: *Epilachna varivestis, Henosepilachna vigintioctopunctata*, etc.,
Tenebrionidae: *Tenebrio molitor, Tribolium castaneum*, etc.,
Meloidae: *Epicauta gorhami*, etc.,
Cerambycidae: *Anoplophora glabripennis, Xylotrechus pyrrhoderus, Monochamus alternatus*, etc.,
Bruchidae: *Callosobruchus chinensis*, etc.,
Chrysomelidae: *Leptinotarsa decemlineata, Diabrotica virgifera, Phaedon brassicae, Phyllotreta striolata*, etc.,
Brentidae: *Cylas formicarius*, etc.,
Curculionidae: *Hypera postica, Listroderes costirostris, Euscepes postfasciatus*, etc.,
Erirhinidae: *Echinocnemus bipunctatus, Lissorhoptrus oryzophilus*, etc.,
Dryophthoridae: *Sitophilus zeamais, Sphenophrus venatus*, etc.,
Scolytidae: *Tomicus piniperda*, etc.,
Platypodidae: *Crossotarsus niponicus*, etc.,
Lyctidae: *Lyctus brunneus*, etc.

Diptera pests can be, for example,
Tipulidae: *Tipila aino*, etc.,
Bibionidae: *Plecia nearctica*, etc.,
Mycetophidae: *Exechia shiitakevora*, etc.,
Sciaridae: *Pnyxia scabiei*, etc.,
Cecidomyiidae: *Asphondylia yushimai, Mayetiola destructor*, etc.,
Culicidae: *Aedes aegypti, Culex pipiens pallens*, etc.,
Simuliidae: *Simulim takahasii*, etc.,
Chironomidae: *Chironomus oryzae*, etc.,
Tabanidae: *Chrysops suavis, Tabanus trigonus*, etc.,
Syrphidae: *Eumerus strigatus*, etc.,
Tephritidae: *Bactrocera dorsalis, Euphranta japonia, Ceratitis capitata*, etc.,
Agromyzidae: *Liriomyza trifolii, Chromatomyia horticola*, etc.,
Chloropidae: *Meromyza nigriventris*, etc., Drosophilidae: *Drosophila suzukii, Drosophila melanogaster*, etc.,
Ephydridae: *Hydrellia griseola*, etc.,
Hippoboscidae: *Hippobosca equina*, etc.,
Scatophagidae: *Parallelpmma sasakawae*, etc.,
Anthomyiidae: *Delia antiqua, Delia platura*, etc.,
Fanniidae: *Fannia canicularis*, etc.,
Muscidae: *Musca domestica, Stomoxys calcitrans*, etc.,
Sarcophagidae: *Sarcophaga peregrina*, etc.,
Gasterophilidae: *Gasterophilus intestinalis*, etc.,
Hypodermatidae: *Hypoderma lineatum*, etc.,
Oestridae: *Oestrus ovis*, etc.
  Lepidoptera pests can be, for example,
Hepialidae: *Endoclita excrescens*, etc.,
Heliozelidae: *Antispila ampelopsia*, etc.,
Cossidae: *Zeuzera leuconotum*, etc.,
Tortricidae: *Archips fuscocupreanus, Adoxophyes orana fasciata, Grapholita molesta, Homona magnanima, Leguminivora glycinivorella, Cydia pomonella*, etc.,
Cochylidae: *Eupoecilia ambiguella*, etc.,
Psychidae: *Bambalina* sp., *Eumeta minuscula*, etc.,
Tineidae: *Nemapogon granella, Tinea translucens*, etc.,
Bucculatricidae: *Bucculatrix pyrivorella*, etc.,
Lyonetiidae: *Lyonetia clerkella*, etc.,
Gracilariidae: *Caloptilia theivora, Phyllonorycter ringoniella*, etc.,
Phyllocnistidae: *Phyllocnistis citrella*, etc.,
Acrolepiidae: *Acrolepiopsis sapporensis*, etc.,
Yponomeutidae: *Plutella xylostella, Yponomeuta orientalis*, etc.,
Argyresthidae: *Argyresthia conjugella*, etc.,
Sesidae: *Nokona regalis*, etc.,
Gelechiidae: *Phthorimaea operculella, Sitotroga cerealella, Pectinophora gossypiella*, etc.,
Carposinidae: *Carposina sasakii*, etc.,
Zygaenidae: *Illiberis pruni*, etc.,
Limacodidae: *Monema flavescens*, etc.,
Crambidae: *Ancylolomia japonica, Chilo suppressalis, Cnaphalocrosis medinalis, Ostrinia furnacalis, Ostrinia nubilalis*, etc.,
Pyralidae: *Cadra cautella, Galleria mellonella*, etc.,
Pterophoridae: *Nippoptilia vitis*, etc.,
Papilionidae: *Papilio xuthus*, etc.,
Pieridae: *Pieris rapae*, etc.,
Hesperiidae: *Parnara guttata guttata*, etc.,
Geometridae: *Ascotis selenaria*, etc.,
Lasiocampidae: *Dendrolimus spectabilis, Malacosomaneustrium testaceum*, etc.,
Sphingidae: *Agrius convolvuli*, etc.,
Lymantriidae: *Arna pseudoconspersa, Lymantria dispar*, etc.,
Arctiidae: *Hyphantria cunea*, etc.,
Noctuidae: *Agrotis ipsilon, Autographa nigrisigna, Helicoverpa armigera, Helicoverpa zea, Heliothis virescens, Spodoptera exigua, Spodoptera litura*, etc.
  Hymenoptera pests can be, for example,
Argidae: *Arge pagana*, etc.,
Tenthredinidae: *Apethymus kuri, Athalia rosae ruficornis*, etc.,
Cynipidae: *Dryocosmus kuriphilus*, etc.,
Vespidae: *Vespa simillima xanthoptera*, etc.,
Formicidae: *Solenopsis invicta*, etc.,
Megachilidae: *Megachile nipponica*, etc.
  Order Collembola pests can be, for example,
Sminthuridae: *Bourletiella hortensis*, etc.
  Order Thysanura pests can be, for example,
Lepismatidae: *Lepisma saccharina, Ctenolepisma villosa*, etc.
  Blattodea pests can be, for example,
Blattidae: *Periplaneta americana*,
Blattellidae: *Blattella germanica*, etc.
  Order Isoptera pests can be, for example,
Kalotermitidae: *Incisitermes minor*, etc.,
Rhinotermitidae: *Coptotermes formosanus*, etc.,
Termitidae: *Odontotermes formosanus*, etc.
  Order Psocoptera pests can be, for example
Trogiidae: *Trogium pulsatorium*, etc.,
Liposcelididae: *Liposcelis corrodens*, etc.
  Order Mallohaga pests can be, for example,
Menoponidae: *Lipeurus caponis*, etc.,
Trichodectidae: *Damalinia bovis*, etc.
  Order Anoplura pests can be, for example,
Haematopinidae: *Haematopinus suis*, etc.,
Pediculine: *Pediculus humanus*, etc.,
Linognathidae: *Linognathus setosus*, etc.,
Pthiridae: *Phthrius pubis*, etc.
  Plant-feeding mites can be, for example,
Eupodidae: *Penthaleus major*, etc.,
Tarsonemidae: *Phytonemus pallidus, Polyphagotarsonemus latus*, etc.,
Pyemotidae: *Siteroptes* sp., etc.,
Tenuipalpidae: *Brevipalpus lewisi*, etc.,
Tuckerellidae: *Tuckerella pavoniformis*, etc.,
Tetranychidae: *Eotetranychus boreus, Panonychus citri, Panonychus ulmi, Tetranychus urticae, Tetranychus kanzawai*, etc.,
Nalepellidae: *Trisetacus pini*, etc.,
Eriophyidae: *Aculops pelekassi, Epitrimerus pyri, Phyllocoptruta oleivola*, etc.,
Diptilomiopidae: *Diptacus crenatae*, etc.,
Acaridae: *Aleuroglyphus ovatus, Tyrophagus putrescentiae, Rhizoglyphus robini*, etc.
  Plant-parasitic nematodes can be, for example,
Longidoridae: *Xiphinema index*, etc.,
Trichodoridae: *Paratrichodorus minor*, etc.,
Rhabditidae: *Rhabditella* sp., etc.,
Tylenchidae: *Aglenchus* sp., etc.,
Tylodoridae: *Cephalenchus* sp., etc.,
Anguinidae: *Nothotylenchus acris, Ditylenchus destructor*, etc.,
Hoplolaimidae: *Rotylenchulus reniformis, Helicotylenchus dihystera*, etc.,
Paratylenchidae: *Paratylenchus curvitatus*, etc.,
Meloidogynidae: *Meloidogyne incognita, Meloidogyne hapla*, etc.,
Heteroderidae: *Globodera rostochiensis, Heterodera glycines*, etc.,
Telotylenchidae: *Tylenchorhynchus claytoni* etc.,
Psilenchidae: *Psilenchus* sp., etc.,
Criconematidae: *Criconemoides* sp., etc.,
Tylenchulidae: *Tylenchulus semipenetrans*, etc.,
Spaeronematidae: *Sphaeronema camelliae*, etc.,
Pratylenchidae: *Sphaeronema camelliae, Radopholus citrophilus, Radopholus similis, Nacobbus aberrans, Pratylenchus penetrans, Pratylenchus coffeae*, etc.,
Iotonchiidae: *Iotonchium ungulatum*, etc.,
Aphelenchidae: *Aphelenchus avenae*, etc.,
Aphelenchoididae: *Aphelenchoides besseyi, Aphelenchoides fragariae*, etc.,
Palasitaphelenchidae: *Bursaphelenchus xylophilus*, etc.
  Plant-parasitic mollusc pests can be, for example,
Pilidae: *Pomacea canaliculata*, etc.,
Veronicellidae: *Leavicaulis alte*, etc., Achatinidae: *Achatina fulica*, etc.,
Philomycidae: *Meghimatium bilineatum*, etc.,
Succineidae: *Succinea lauta*, etc.,
Didcidae: *Discus pauper*, etc.,
Zonitidae: *Zonitoides yessoensis*, etc.,
Limacidae: *Limax flavus, Deroceras reticulatum*, etc.,
Helicarionidae: *Parakaliella harimensis*, etc.,
Bradybaenidae: *Acusta despecta sieboldiana, Bradybaena similaris*, etc.

Other pests such as injurious animals, uncomfortable animals, sanitary insects, livestock insects, parasites and the like can be, for example,
Acari Macronysshidae: *Ornithonyssus sylvialum*, etc.,
Varroidae: *Varroa jacobsoni*, etc.,
Dermanyssidae: *Dermanyssus gallinae*, etc.,
Macronyssidae: *Ornithonyssus sylvialum*, etc.,
Ixodidae: *Boophilus microplus, Rhipicephalus sanguineus, Haemaphysalis longicornis*, etc.,
Sacroptidae: *Sarcoptes scabiei*, etc.,
Isopoda Armadillidiidae: *Armadillidium vulgare*, etc.,
Decapoda Astacidae: *Procambarus clarkii*, etc.,
Porcellionidae: *Armadillidium vulgare*, etc.,
Chilopoda pests: *Scutigeromorpha Sutigeridae, Thereuonema tuberculata, Scolopendromorpha Scolopendra subpinipes*, etc.
Diplopoda pests: *Polydesmida Paradoxosomatidae Oxidus gracillis*, etc.
Araneae Latrodectus hasseltii: *Theridiiadae hasseltii*, etc.,
Clubionidae: *Chiracanthium japonicum*, etc.,
Order Scorpionida: *Androctonus crassicauda*, etc.,
Parasitic roundworm: *Ascaris lumbricoides, Syphacia* sp., *Wucherebia bancrofti*, etc.,
Parasitic flatworm: *Distomum* sp., *Paragonimus westermanii, Metagonimus yokokawai, Schistosoma japonicum, Taenia solium, Taeniarhynchus saginatus, Echinococcus* sp., *Diphyllobothrium latum*, etc.

The present pest control agent also exhibits control effect to the above-mentioned pests, etc., which already have resistance to existing pest control agents. Further, the present control agent can be applied to plants which already have resistance to insects, diseases, herbicides, etc., owing to genetic modification and artificial mating, etc.

Next, there are details and descriptions about the production methods, formulation methods and applications of the present compound in the form of examples. However, the present invention is not only restricted by these examples.

There are also descriptions about the production methods of intermediates for the production of the present compound.

EXAMPLES

The present invention describes in more details with reference to the following Preparation Examples, Formulation Example and Test Examples. However, the present invention is not limited to these Examples. In addition, alterations can be made within the scope that does not depart from the scope of the present invention.

Preparation Example 1

Preparation of 3-(2-fluoro-4-methyl-5-((2,2,2-trifluoroethyl)thio)phenyl)-5-(trifluoromethyl)isoxazole (compound 1)

(1) 4,4,4-trifluoro-1-(2-fluoro-4-methyl-5-((2,2,2-trifluoroethyl)thio)phenyl)butane-1,3-dione To a THF (100 mL) solution of 1-(5-(2,2,2-trifluoroethylthio)-2-fluoro-4-methylphenyl)ethanone (10.0 g, 37.0 mmol) was added NaH (60% in mineral oil, 2.20 g, 55.0 mmol) in three portions maintaining the temperature between 0 to 10° C. After stirring at this temperature for 20 min., ethyl trifluoroacetate (7.88 g, 55.0 mmol) was slowly added and the reaction mixture was allowed to stir at room temperature for 1 h. The reaction mixture was then poured into ice water, acidified with 2M HCl solution, and extracted with ethyl acetate (3×100 mL). The combined organic layers were then washed with distilled water (2×100 mL), dried over sodium sulfate and concentrated under reduced pressure to get crude product (14.0 g). The crude product thus obtained was further used without any purification.

$^1$H NMR (CDCl$_3$): 8.13 (d, J=6.8 Hz, 1H), 7.09 (d, J=12.4 Hz, 1H), 6.68 (m, 1H), 3.39 (q, J=9.6 Hz, 2H), 2.54 (s, 3H).

(2) 3-(2-fluoro-4-methyl-5-((2,2,2-trifluoroethyl)thio)phenyl)-5-(trifluoromethyl)-4,5-dihydroisoxazol-5-ol To an ethanol (25 mL) solution of 4,4,4-trifluoro-1-(2-fluoro-4-methyl-5-((2,2,2-trifluoroethyl)thio)phenyl)butane-1,3-dione (1.0 g, 2.70 mmol) was added hydroxylamine hydrochloride (0.29 g, 4.10 mmol) at 10° C., and the mixture was then stirred for 3 h at 80° C. After distillation of ethanol, the residue was extracted with ethyl acetate (3×10 mL). The combined organic layer was washed with brine, dried over sodium sulfate, filtered and concentrated under reduced pressure to get crude product. The residue was then purified by column chromatography(ethyl acetate:n-hexane=1:2) to afford 3-(2-fluoro-4-methyl-5-((2,2,2-trifluoroethyl)thio)phenyl)-5-(trifluoromethyl)-4,5-dihydroisoxazol-5-ol (0.45 g, Yield 43.2%).

$^1$H NMR (CDCl$_3$): 8.05 (d, J=7.2 Hz, 1H), 7.05 (d, J=11.6 Hz, 1H), 3.75-3.80 (m, 1H), 3.55-3.63 (m, 1H), 3.38 (q, J=9.6 Hz, 2H), 2.51 (s, 3H).

(3) 3-(2-fluoro-4-methyl-5-((2,2,2-trifluoroethyl)thio)phenyl)-5-(trifluoromethyl)isoxazole (compound 1)

To a toluene (80 mL) solution of 3-(2-fluoro-4-methyl-5-((2,2,2-trifluoroethyl)thio)phenyl)-5-(trifluoromethyl)-4,5-dihydroisoxazol-5-ol (6.50 g, 17.0 mmol) was added thionyl chloride (3.07 g, 26.0 mmol) and pyridine (5.36 g, 68.0 mmol) at room temperature. The mixture was then heated at 100° C. for 1 h. After cooling to room temperature, the reaction mixture was extracted with dichloromethane (3×100 mL). The combined organic layers were then washed with brine, dried over sodium sulfate, filtered and concentrated under reduced pressure. The residue was then purified by column chromatography (ethyl acetate:n-hexane=1:4) to afford 3-(2-fluoro-4-methyl-5-((2,2,2-trifluoroethyl)thio)phenyl)-5-(trifluoromethyl)isoxazole (6.10 g, Yield 98.5%).

$^1$H NMR (CDCl$_3$): 8.18 (d, J=7.2 Hz, 1H), 7.11-7.14 (m, 2H), 3.40 (q, J=9.6 Hz, 2H), 2.54 (s, 3H).

Preparation Example 2

Preparation of 3-(2-fluoro-4-methyl-5-((2,2,2-trifluoroethyl)thio)phenyl)-4-methyl-5-(trifluoromethyl)isoxazole (compound 37)

(1) 2-fluoro-N-methoxy-N,4-dimethylbenzamide

To a dichloromethane (200 mL) solution of 2-fluoro-4-methylbenzoic acid (20.0 g, 130 mmol) added N,O-dimethylhydroxylamine (18.9 g, 190 mmol), N-(3-Dimethylaminopropyl)-N-ethylcarbodiimide hydrochloride (37.3 g, 190 mmol), 1-Hydroxybenzotriazole hydrate (26.3 g, 190 mmol) and diisopropylethylamine (72 mL, 390 mmol) at 0° C. The reaction mixture was then stirred at room temperature for 1 h. The reaction mixture was then poured into ice water, and extracted with ethyl acetate (3×100 ml). The combined organic layers were then washed with distilled water (2×100 mL), dried over sodium sulfate and concentrated under reduced pressure to get crude product (22.0 g, 86%). The crude product thus obtained was further used without any purification.

$^1$H NMR (CDCl$_3$): 7.32 (t, J=7.6 Hz, 1H), 6.99 (d, J=7.6 Hz, 1H), 6.91 (d, J=10.8 Hz, 1H), 3.57 (s, 3H), 3.33 (s, 3H), 2.37 (s, 3H).

(2) 1-(2-fluoro-4-methylphenyl)propan-1-one

To an anhydrous THF (150 ml) solution of 2-fluoro-N-methoxy-N,4-dimethylbenzamide (8.0 g, 40.0 mmol) was added dropwise ethylmagnesium bromide (80 mL, 80.0 mmol, 1M solution in THF) at 0° C. The reaction mixture was then stirred at room temperature for 3 h. The reaction mixture was then poured into ice water, and extracted with ethyl acetate (3×100 mL). The combined organic layers were then washed with distilled water (2×100 mL), dried over sodium sulfate and concentrated under reduced pressure to get crude product (3.20 g, 48%). The crude product thus obtained was further used without any purification.

$^1$H NMR (CDCl$_3$): 7.78 (t, J=8.0 Hz, 1H), 7.02 (d, J=8.0 Hz, 1H), 6.93 (d, J=12 Hz, 1H), 2.94-2.99 (m, 2H), 1.19 (t, J=7.2 Hz, 3H).

(3) 4,4,4-trifluoro-1-(2-fluoro-4-methylphenyl)-2-methylbutane-1,3-dione

To an anhydrous THF (60 mL) of 1-(2-fluoro-4-methylphenyl)propan-1-one (5.0 g, 30.0 mmol) was added dropwise Lithium bis(trifluoromethylsilyl)amide (7.5 g, 45.0 mmol) at −20° C. After stirring at this temperature for 30 min., ethyl trifluoroacetate (6.41 g, 45.0 mmol) was slowly added at −20° C. The reaction mixture was allowed to stir at room temperature for 6 h.

The reaction mixture was then poured into ice water, acidified with 2M HCl solution, and extracted with ethyl acetate (3×80 ml). The combined organic layers were then washed with distilled water (2×50 mL), dried over sodium sulfate and concentrated under reduced pressure to get crude product (7.2 g). The crude product thus obtained was further used without any purification (377 (M+H), 46% purity by LC-MS).

(4) 3-(2-fluoro-4-methylphenyl)-4-methyl-5-(trifluoromethyl)-4,5-dihydroisoxazol-5-ol To an ethanol (50 mL) solution of 4,4,4-trifluoro-1-(2-fluoro-4-methylphenyl)-2-methylbutane-1,3-dione(7.2 g, 27.0 mmol) was added hydroxylamine hydrochloride (3.81 g, 54.0 mmol) at room temperature, and the mixture was then refluxed for 3 h at 80° C. After distillation of ethanol, the residue was extracted with ethyl acetate (3×100 mL). The combined organic layers were washed with brine, dried over sodium sulfate, filtered and concentrated under reduced pressure to get crude product. The residue was then purified by chromatography (ethyl acetate:n-hexane=1:1) to afford 3-(2-fluoro-4-methylphenyl)-4-methyl-5-(trifluoromethyl)-4,5-dihydroisoxazol-5-ol (3.0 g, Yield 39%).

$^1$H NMR (CDCl$_3$): 7.55 (t, J=8.0 Hz, 1H), 7.30 (d, J=8.0 Hz, 1H), 6.98 (d, J=12.4 Hz, 1H), 3.98-4.07 (m, 1H), 3.32 (bs, 1H), 2.40 (s, 3H), 1.26 (d, J=7.6 Hz, 3H).

(5) 3-(2-fluoro-4-methylphenyl)-4-methyl-5-(trifluoromethyl)isoxazole

To a toluene (20 mL) solution of 3-(2-fluoro-4-methylphenyl)-4-methyl-5-(trifluoromethyl)-4,5-dihydroisoxazol-5-ol (3.0 g, 10.8 mmol) under N2 was added thionyl chloride (2.03 g, 16.2 mmol) and pyridine (6.61 g, 54.0 mmol) at 0° C. The mixture was then heated at 100° C. for 1 h. After cooling to room temperature, the reaction mixture was extracted with dichloromethane (3×80 mL). The combined organic layers were then washed with brine, dried over sodium sulfate, filtered and concentrated under reduced pressure. The residue was then purified by chromatography (ethyl acetate:n-hexane=1:4) to afford 3-(2-fluoro-4-methylphenyl)-4-methyl-5-(trifluoromethyl)isoxazole (2.0 g, Yield 71%).

$^1$H NMR (CDCl$_3$): 7.39 (t, J=7.6 Hz, 1H), 7.09 (d, J=7.6 Hz, 1H), 7.04 (d, J=10.8 Hz, 1H), 2.43 (s, 3H), 2.13 (t, J=2.0 Hz, 3H).

(6) 4-fluoro-2-methyl-5-(4-methyl-5-(trifluoromethyl) isoxazol-3-yl)benzenesulfonyl chloride Chlorosulfonic acid (4.49 g, 38.6 mmol) was slowly added to 3-(2-fluoro-4-methylphenyl)-4-methyl-5-(trifluoromethyl)isoxazole (2.0 g, 7.71 mmol) keeping the temperature of the reaction mixture below 30° C. The resulting mixture was then heated to 70° C. for 4 h. After cooling to room temperature, the reaction mixture was then poured carefully into ice, the precipitate was filtered, washed well with distilled water and dried to get 0.80 g of crude product. The crude product thus obtained was further used without any purification.

$^1$H NMR (CDCl$_3$): 8.30 (d, J=6.8 Hz, 1H), 7.32 (d, J=10 Hz, 1H), 2.88 (s, 3H), 2.16 (t, J=2.0 Hz, 3H).

(7) 4-fluoro-2-methyl-5-(4-methyl-5-(trifluoromethyl)isoxazol-3-yl)benzenethiol

To a stirred solution of 4-fluoro-2-methyl-5-(4-methyl-5-(trifluoromethyl)isoxazol-3-yl)benzenesulfonyl chloride (0.80 g, 2.23 mmol) in toluene (20 mL) was added triphenylphosphine (2.34 g, 8.90 mmol) at 0° C. under N2. The reaction mixture was then heated at 100° C. for 1 h. After completion of the reaction, the reaction mixture was cooled to room temperature, and then added 1N NaOH solution (20 ml). After layer separation, aqueous layer was washed with ethyl acetate (3×50 mL). The aqueous layer was then acidified with 6N HCl solution (30 mL). The obtained precipitate was collected by filtration, washed with distilled water (3×50 mL) and dried under vacuum to afford title product as a white solid (0.16 g, Yield 22%). The crude product thus obtained was further used without any purification.

$^1$H NMR (CDCl$_3$): 7.44 (d, J=6.8 Hz, 1H), 7.07 (d, J=10.4 Hz, 1H), 3.49 (s, 1H), 2.41 (s, 3H), 2.13 (t, J=2.0 Hz, 3H).

(8) 3-(2-fluoro-4-methyl-5-((2,2,2-trifluoroethyl) thio)phenyl)-4-methyl-5-(trifluoromethyl)isoxazole (compound 37)

A dimethylformamide (4 mL) solution of 4-fluoro-2-methyl-5-(4-methyl-5-(trifluoromethyl)isoxazol-3-yl)benzenethiol (0.140 g, 0.48 mmol) was cooled to 0° C. To it were sequentially added potassium carbonate (0.10 g, 0.72 mmol) and trifluoroethyl iodide (0.201 g, 0.96 mmol) and the resulting mixture was then stirred at room temperature for 6 h. The reaction mixture was then poured into distilled water and extracted with dichloromethane (3×25 mL). The combined organic layers were washed with distilled water, dried over sodium sulfate, filtered and concentrated under reduced pressure to get crude product. The residue was then purified by column chromatography (ethyl acetate:n-hexane=1:5) to afford 3-(2-fluoro-4-methyl-5-((2,2,2-trifluoroethyl)thio)phenyl)-4-methyl-5-(trifluoromethyl)isoxazole (0.082 g, Yield 45.7%)

$^1$H NMR (CDCl$_3$): 7.67 (d, J=7.2 Hz, 1H), 7.14 (d, J=10.4 Hz, 1H), 3.37 (q, J=9.2 Hz, 2H), 2.56 (s, 3H), 2.13 (t, J=2.0 Hz, 3H).

Preparation Example 3

Preparation of 3-(2-fluoro-4-methyl-5-((2,2,2-trifluoroethyl)sulfinyl)phenyl)-5-(trifluoromethyl)isoxazole (compound 2)

m-CPBA (70% purity, 4.19 g, 17.0 mmol) was added to a solution of 3-(2-fluoro-4-methyl-5-((2,2,2-trifluoroethyl)thio)phenyl)-5-(trifluoromethyl)isoxazole (6.10 g, 17.0 mmol) in dichloromethane (70 mL) at −5 to 0° C. The reaction mixture was stirred for 30 min at −5 to 10° C. before being quenched with sat. NaHCO$_3$ solution (70 mL). The layers were separated, and the aqueous partition was extracted with dichloromethane (3×75 mL). The combined organic layers were washed with sat. NaHCO$_3$ solution (2×50 mL) and dried over sodium sulfate and the solvent was removed under reduced pressure. The residue was then purified by column chromatography (ethyl acetate:n-hexane=1:1) to afford 3-(2-fluoro-4-methyl-5-((2,2,2-trifluoroethyl)sulfinyl)phenyl)-5-(trifluoromethyl)isoxazole (6.0 g, Yield 94.3%) as a white solid.

$^1$H NMR (CDCl$_3$): 8.61 (d, J=7.2 Hz, 1H), 7.15-7.19 (m, 2H), 3.43-3.55 (m, 2H), 2.84 (s, 3H).

Preparation Example 4

Preparation of 3-(2-fluoro-4-methyl-5-((2,2,2-trifluoroethyl)sulfonyl)phenyl)-5-(trifluoromethyl)isoxazole (compound 3)

m-CPBA (70% purity, 0.208 g, 0.84 mmol) was added to a solution of 3-(2-fluoro-4-methyl-5-(2,2,2-trifluoroethyl)thio)phenyl)-5-(trifluoromethyl)isoxazole (0.100 g, 0.28 mmol) in dichloromethane (5 mL) at −5 to 0° C. The reaction mixture was stirred for 24 h at room temperature before being quenched with sat. NaHCO$_3$ solution (10 mL). The layers were separated, and the aqueous partition was extracted with dichloromethane (3×25 mL). The combined organic layers were washed with sat. NaHCO$_3$ solution (2×20 mL) and dried over sodium sulfate and the solvent was removed under reduced pressure. The residue was then purified by column chromatography (dichloromethane:n-hexane=1:1) to afford 3-(2-fluoro-4-methyl-5-((2,2,2-trifluoroethyl)sulfonyl)phenyl)-5-(trifluoromethyl)isoxazole (0.053 g, Yield 49%) as a white solid.

$^1$H NMR (CDCl$_3$): 8.73 (d, J=7.2 Hz, 1H), 7.26-7.28 (m, 1H), 7.16 (d, J=2.8 Hz, 1H), 3.97 (q, J=8.8 Hz, 2H), 2.78 (s, 3H).

Preparation Example 5

Preparation of 3-(2-chloro-4-methyl-5-((2,2,2-trifluoroethyl)thio)phenyl)-5-(trifluoromethyl)isoxazole (compound 22)

(1) 4-Chloro-2-methyl-5-(5-(trifluoromethyl)isoxazol-3-yl)benzenesulfonyl chloride Chlorosulfonic acid (11.1 g, 95.5 mmol) was slowly added to 3-(2-chloro-4-methylphenyl)-5-(trifluoromethyl)isoxazole (5.0 g, 19.1 mmol) keeping the temperature of the reaction mixture below 30° C. The resulting mixture was then heated to 80° C. for 18 h. After cooling to room temperature, the reaction mixture was then poured carefully into ice, the precipitate was filtered, washed well with distilled water and dried to get 6.1 g of crude product. The crude product thus obtained was further used without any purification.

$^1$H NMR (CDCl$_3$): 8.48 (s, 1H), 7.63 (s, 1H), 7.21 (s, 1H), 2.84 (s, 3H).

(2) 4-Chloro-2-methyl-5-(5-(trifluoromethyl)isoxazol-3-yl)benzenethiol

To a mixture of 4-chloro-2-methyl-5-(5-(trifluoromethyl)isoxazol-3-yl)benzenesulfonyl chloride (6.1 g, 16.9 mmol) in glacial acetic acid (60 mL) was portion-wise added zinc dust (5.5 g, 84.5 mmol) at room temperature. The resulting mixture was then refluxed for 4 h. After cooling to room temperature, the reaction mixture was diluted with distilled water and ethyl acetate and filtered through celite bed. The organic layer was washed well by distilled water, dried over sodium sulfate, filtered and concentrated under reduced pressure to get 3.89 g of crude product as pale yellow solid. The crude product thus obtained was further used without any purification.

$^1$H NMR (CDCl$_3$): 7.69 (s, 1H), 7.32 (s, 1H), 7.19 (s, 1H), 3.43 (s, 1H), 2.37 (s, 3H).

(3) 3-(2-Chloro-4-methyl-5-((2,2,2-trifluoroethyl)thio)phenyl)-5-(trifluoromethyl)isoxazole (compound 22)

A dimethylformamide (20 mL) solution of 4-chloro-2-methyl-5-(5-(trifluoromethyl)isoxazol-3-yl)benzenethiol (3.89 g, 13.2 mmol) was cooled to 0° C. To the cooled solution were sequentially added potassium carbonate (2.7 g, 19.8 mmol) and trifluoroethyl iodide (5.3 g, 19.8 mmol) and the resulting mixture was then stirred at room temperature for 6 h. The reaction mixture was then poured into distilled water and extracted with dichloromethane (3×25 mL). The combined organic layers were washed with distilled water, dried over sodium sulfate, filtered and concentrated under reduced pressure to get crude product. The residue was then purified by column chromatography (ethyl acetate:n-hexane=1:5) to afford 3-(2-Chloro-4-methyl-5-((2,2,2-trifluoroethyl)thio)phenyl)-5-(trifluoromethyl)isoxazole (3.90 g, Yield 78.8%).

$^1$H NMR (CDCl$_3$): 7.87 (s, 1H), 7.40 (s, 1H), 7.12 (s, 1H), 3.44 (q, J=9.6 Hz, 2H), 2.50 (s, 3H).

Preparation Example 6

Preparation of 3-(2-chloro-4-methyl-5-((2,2,2-trifluoroethyl)sulfinyl)phenyl)-5-(trifluoromethyl)isoxazole (compound 23)

m-CPBA (65% purity, 0.212 g, 0.798 mmol) was added to a solution of 3-(2-chloro-4-methyl-5-((2,2,2-trifluoroethyl)

thio)phenyl)-5-(trifluoromethyl)isoxazole (0.300 g, 0.798 mmol) in dichloromethane (25 mL) at −5 to 0° C. The reaction mixture was stirred for 30 min at −5 to 10° C. before being quenched with sat. NaHCO₃ solution (70 mL). The layers were separated, and the aqueous partition was extracted with dichloromethane (3×25 mL). The combined organic layers were washed with sat. NaHCO₃ solution (2×50 mL) and dried over sodium sulfate and the solvent was removed under reduced pressure. The residue was then purified by column chromatography (ethyl acetate:n-hexane=1:1) to afford 3-(2-Chloro-4-methyl-5-((2,2,2-trifluoroethyl)sulfinyl)phenyl)-5-(trifluoromethyl)isoxazole (0.280 g, Yield 90.0%) as a white solid.

¹H NMR (CDCl₃): 8.34 (s, 1H), 7.47 (s, 1H), 7.10 (s, 1H), 3.40-3.52 (m, 2H), 2.46 (s, 3H).

Representative compounds of the present invention are exemplified in the following Table 1, but the present invention is not limited to these compounds.

The compounds shown in Table 1, other than the compounds obtained in Preparation Examples 1 to 6, were produced by methods similar to the methods described in Preparation examples 1 to 6 or methods described in the description.

The abbreviations in Table 1 are as indicated below.
F: fluoro, Cl: chloro, Me: methyl, CF₃: trifluoromethyl, CF₂CF₃: pentafluoroethyl, CF₂CF₂CF₃: heptafluoropropyl, CF₂CF₂CF₂CF₃: nonafluorobutyl, CHF₂: difluoromethyl, CF₂Cl: chlorodifluoromethyl, Ph: phenyl, CF₂Ph: difluoro(phenyl)methyl.

TABLE 1

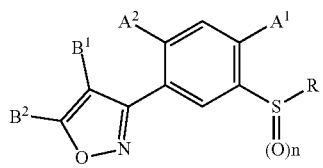

(I)

| No | R | A¹ | A² | B¹ | B² | n |
|---|---|---|---|---|---|---|
| 1 | CH₂CF₃ | Me | F | H | CF₃ | 0 |
| 2 | CH₂CF₃ | Me | F | H | CF₃ | 1 |
| 3 | CH₂CF₃ | Me | F | H | CF₃ | 2 |
| 4 | CH₂CF₃ | Me | F | H | CF₂CF₃ | 0 |
| 5 | CH₂CF₃ | Me | F | H | CF₂CF₃ | 1 |
| 6 | CH₂CF₃ | Me | F | H | CF₂CF₃ | 2 |
| 7 | CH₂CF₃ | Me | F | H | CF₂CF₂CF₃ | 0 |
| 8 | CH₂CF₃ | Me | F | H | CF₂CF₂CF₃ | 1 |
| 9 | CH₂CF₃ | Me | F | H | CF₂CF₂CF₃ | 2 |
| 10 | CH₂CF₃ | Me | F | H | CF₂CF₂CF₂CF₃ | 0 |
| 11 | CH₂CF₃ | Me | F | H | CF₂CF₂CF₂CF₃ | 1 |

TABLE 1-continued

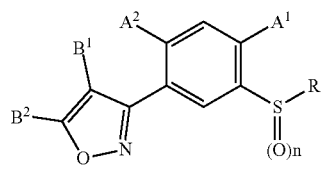

(I)

| No | R | A¹ | A² | B¹ | B² | n |
|---|---|---|---|---|---|---|
| 12 | CH₂CF₃ | Me | F | H | CF₂CF₂CF₂CF₃ | 2 |
| 13 | CH₂CF₃ | Me | F | H | CHF₂ | 0 |
| 14 | CH₂CF₃ | Me | F | H | CHF₂ | 1 |
| 15 | CH₂CF₃ | Me | F | H | CHF₂ | 2 |
| 16 | CH₂CF₃ | Me | F | H | CF₂Cl | 0 |
| 17 | CH₂CF₃ | Me | F | H | CF₂Cl | 1 |
| 18 | CH₂CF₃ | Me | F | H | CF₂Cl | 2 |
| 19 | CH₂CF₃ | Me | F | H | CF₂Ph | 0 |
| 20 | CH₂CF₃ | Me | F | H | CF₂Ph | 1 |
| 21 | CH₂CF₃ | Me | F | H | CF₂Ph | 2 |
| 22 | CH₂CF₃ | Me | Cl | H | CF₃ | 0 |
| 23 | CH₂CF₃ | Me | Cl | H | CF₃ | 1 |
| 24 | CH₂CF₃ | Me | Cl | H | CF₃ | 2 |
| 25 | CH₂CF₃ | Me | Me | H | CF₃ | 0 |
| 26 | CH₂CF₃ | Me | Me | H | CF₃ | 1 |
| 27 | CH₂CF₃ | Me | Me | H | CF₃ | 2 |
| 28 | CH₂CF₃ | F | F | H | CF₃ | 0 |
| 29 | CH₂CF₃ | F | F | H | CF₃ | 1 |
| 30 | CH₂CF₃ | F | F | H | CF₃ | 2 |
| 31 | CH₂CF₃ | Cl | Cl | H | CF₃ | 0 |
| 32 | CH₂CF₃ | Cl | Cl | H | CF₃ | 1 |
| 33 | CH₂CF₃ | Cl | Cl | H | CF₃ | 2 |
| 34 | CH₂CH₂CH₃ | Me | F | H | CF₃ | 0 |
| 35 | CH₂CH₂CH₃ | Me | F | H | CF₃ | 1 |
| 36 | CH₂CH₂CH₃ | Me | F | H | CF₃ | 2 |
| 37 | CH₂CF₃ | Me | F | Me | CF₃ | 0 |
| 38 | CH₂CF₃ | Me | F | Me | CF₃ | 1 |
| 39 | CH₂CF₃ | Me | F | Me | CF₃ | 2 |
| 40 | CH₂CF₃ | Me | Me | H | CF₂Ph | 0 |
| 41 | CH₂CF₃ | Me | Me | H | CF₂Ph | 1 |
| 42 | CH₂CF₃ | Me | Me | H | CF₂Ph | 2 |
| 43 | CH₂CF₃ | Me | Cl | H | CF₂Cl | 0 |
| 44 | CH₂CF₃ | Me | Cl | H | CF₂Cl | 1 |
| 45 | CH₂CF₃ | Me | Cl | H | CF₂Cl | 2 |
| 46 | CH₂CF₃ | Me | Me | H | CHF₂ | 0 |
| 47 | CH₂CF₃ | Me | Me | H | CHF₂ | 1 |
| 48 | CH₂CF₃ | Me | Me | H | CHF₂ | 2 |
| 49 | CH₂CF₃ | Me | Me | H | CF₂Cl | 0 |
| 50 | CH₂CF₃ | Me | Me | H | CF₂Cl | 1 |
| 51 | CH₂CF₃ | Me | Me | H | CF₂Cl | 2 |
| 52 | CH₂CF₃ | Me | Cl | H | CF₂Ph | 0 |
| 53 | CH₂CF₃ | Me | Cl | H | CF₂Ph | 1 |
| 54 | CH₂CF₃ | Me | Cl | H | CF₂Ph | 2 |
| 55 | CH₂CF₃ | Me | Cl | H | CHF₂ | 0 |
| 56 | CH₂CF₃ | Me | Cl | H | CHF₂ | 1 |
| 57 | CH₂CF₃ | Me | Cl | H | CHF₂ | 2 |

TABLE 2

Detail and ¹H-NMR of the compounds synthesized belonging to the Formula (I) of the present invention:

| No. | ¹H-NMR δppm (CDCl₃/TMS) |
|---|---|
| 4 | 8.18 (d, J = 7.2 Hz, 1H), 7.18 (d, J = 3.2 Hz, 1H), 7.13 (d, J = 11.6 Hz, 1H), 3.41 (q, J = 9.6 Hz, 2H), 2.54 (s, 3H) |
| 5 | 8.60 (d, J = 7.2 Hz, 1H), 7.17-7.21 (m, 2H), 3.43-3.55 (m, 2H), 2.48 (s, 3H) |
| 6 | 8.68 (d, J = 7.2 Hz, 1H), 7.24-7.26 (m, 1H), 7.19 (d, J = 2.8 Hz, 1H), 4.16 (q, J = 8.8 Hz, 2H), 2.78 (s, 3H) |
| 7 | 8.19 (d, J = 7.2 Hz, 1H), 7.18 (d, J = 3.2 Hz, 1H), 7.13 (d, J = 11.6 Hz, 1H), 3.41 (q, J = 9.2 Hz, 2H), 2.54 (s, 3H) |
| 8 | 8.61 (d, J = 7.2 Hz, 1H), 7.19-7.21 (m, 1H), 7.17 (bs, 1H), 3.41 (q, J = 9.2 Hz, 2H), 2.54 (s, 3H) |
| 9 | 8.74 (d, J = 7.2 Hz, 1H), 7.29 (bs, 1H), 7.21 (d, J = 2.8 Hz, 1H), 3.97 (q, J = 8.8 Hz, 2H), 2.78 (s, 3H) |

TABLE 2-continued

Detail and ¹H-NMR of the compounds synthesized belonging
to the Formula (I) of the present invention:

| No. | ¹H-NMR δppm (CDCl₃/TMS) |
|---|---|
| 10 | 8.19 (d, J = 7.2 Hz, 1H), 7.18 (d, J = 3.2 Hz, 1H), 7.13 (d, J = 11.6 Hz, 1H), 3.41 (q, J = 9.6 Hz, 2H), 2.54 (s, 3H) |
| 11 | 8.61 (d, J = 7.2 Hz, 1H), 7.19-7.21 (m, 1H), 7.17 (s, 1H), 3.43-3.55 (m, 2H), 2.49 (s, 3H) |
| 12 | 8.74 (d, J = 7.2 Hz, 1H), 7.29 (s, 1H), 7.21 (d, J = 2.8 Hz, 1H), 3.97 (q, J = 8.8 Hz, 2H), 2.78 (s, 3H) |
| 13 | 8.12 (d, J = 7.2 Hz, 1H), 7.13 (d, J = 11.6 Hz, 1H), 6.89 (d, J = 3.6 Hz, 1H), 6.82 (t, J = 53.6 Hz, 1H), 3.41 (q, J = 9.6 Hz, 2H), 2.54 (s, 3H) |
| 14 | 8.59 (d, J = 6.8 Hz, 1H), 7.18 (d, J = 10.8 Hz, 1H), 6.96 (d, J = 3.6 Hz, 1H), 6.84 (t, J = 53.6 Hz, 1H), 3.43-3.53 (m, 2H), 2.48 (s, 3H) |
| 15 | 8.68 (d, J = 6.8 Hz, 1H), 7.26-7.27 (m, 1H), 6.98 (d, J = 3.2 Hz, 1H), 6.84 (t, J = 53.6 Hz, 1H), 3.98 (q, J = 8.8 Hz, 2H), 2.78 (s, 3H) |
| 16 | 8.17 (d, J = 7.2 Hz, 1H), 7.12 (d, J = 11.2 Hz, 1H), 7.06 (d, J = 3.2 Hz, 1H), 3.40 (q, J = 9.2 Hz, 2H), 2.54 (s, 3H) |
| 17 | 8.60 (d, J = 6.8 Hz, 1H), 7.17 (d, J = 10.8 Hz, 1H), 7.08 (d, J = 2.8 Hz, 1H), 3.43-3.54 (m, 2H), 2.48 (s, 3H) |
| 18 | 8.72 (d, J = 7.2 Hz, 1H), 7.28 (bs, 1H), 7.08 (d, J = 3.2 Hz, 1H), 3.97 (q, J = 8.8 Hz, 2H), 2.78 (s, 3H) |
| 19 | 8.14 (d, J = 7.2 Hz, 1H), 7.62-7.64 (m, 2H), 7.47-7.53 (m, 3H), 7.09 (d, J = 11.2 Hz, 1H), 6.90 (d, J = 3.2 Hz, 1H), 3.38 (q, J = 9.6 Hz, 2H), 2.52 (s, 3H) |
| 20 | 8.54 (d, J = 7.2 Hz, 1H), 7.62-7.64 (m, 2H), 7.48-7.54 (m, 3H), 7.14 (d, J = 10.8 Hz, 1H), 6.92 (d, J = 3.2 Hz, 1H), 3.38-3.51 (m, 2H), 2.47 (s, 3H) |
| 21 | 8.67 (d, J = 6.8 Hz, 1H), 7.62-7.64 (m, 2H), 7.48-7.54 (m, 3H), 7.22 (bs, 1H), 6.92 (d, J = 3.2 Hz, 1H), 3.95 (q, J = 8.8 Hz, 2H), 2.76 (s, 3H) |
| 22 | 7.87 (s, 1H), 7.40 (s, 1H), 7.20 (d, J = 0.8 Hz, 1H), 3.44 (q, J = 9.5 Hz, 2H), 2.51 (s, 3H) |
| 23 | 8.34 (s, 1H), 7.47 (s, 1H), 7.18 (d, J = 0.8 Hz, 1H), 3.41-3.59 (m, 2H), 2.46 (s, 3H) |
| 24 | 8.44 (s, 1H), 7.58 (s, 1H), 7.19 (d, J = 0.8 Hz, 1H), 3.97 (q, J = 8.8 Hz, 2H), 2.76 (s, 3H) |
| 25 | 7.64 (s, 1H), 7.22 (s, 1H), 6.88 (d, J = 0.9 Hz, 1H), 3.37 (q, J = 9.6 Hz, 2H), 2.50 (s, 3H) and 2.45 (s, 3H) |
| 26 | 8.07 (s, 1H), 7.38 (s, 1H), 6.96 (d, J = 0.8 Hz, 1H), 3.95 (q, J = 8.9 Hz, 2H), 2.73 (s, 3H) and 2.60 (s, 3H) |
| 27 | 8.15 (s, 1H), 7.38 (s, 1H), 6.96 (d, J = 0.8 Hz, 1H), 3.95 (q, J = 8.9 Hz, 2H), 2.73 (s, 3H) and 2.60 (s, 3H) |
| 28 | 8.27 (t, J = 8.0 Hz, 1H), 7.12 (d, J = 0.8 Hz, 1H), 7.04-7.09 (m, 1H), 3.43 (q, J = 9.6 Hz, 2H) |
| 29 | 8.56 (t, J = 7.6 Hz, 1H), 7.13-7.18 (m, 2H), 3.60-3.71 (m, 2H) |
| 30 | 8.41 (t, J = 7.6 Hz, 1H), 8.04-8.09 (m, 2H), 5.13 (q, J = 9.6 Hz, 2H) |
| 31 | 7.64 (bs, 1H), 7.65 (bs, 1H), 7.19 (d, J = 0.8 Hz, 1H), 3.53 (q, J = 9.2 Hz, 2H) |
| 32 | 8.34 (s, 1H), 7.68 (s, 1H), 7.18 (bs, 1H), 3.44-3.53 (m, 2H) |
| 33 | 8.56 (s, 1H), 7.82 (s, 1H), 7.20 (bs, 1H), 4.25 (q, J = 8.8 Hz, 2H) |
| 34 | 7.88 (d, J = 7.2 Hz, 1H), 7.13 (d, J = 3.2 Hz, 1H), 7.05 (d, J = 11.2 Hz, 1H), 2.92 (t, J = 7.2 Hz, 2H), 2.42 (s, 3H), 1.69-1.75 (m, 2H), 1.05 (t, J = 7.2 Hz, 3H) |
| 35 | 8.48 (d, J = 7.2 Hz, 1H), 7.14 (d, J = 2.0 Hz, 1H), 7.11 (d, J = 11.2 Hz, 1H), .75-2.79 (m, 2H), 2.44 (s, 3H), 1.84-1.92 (m, 1H), 1.71-1.78 (m, 1H), 1.08 (t, J = 7.2 Hz, 3H) |
| 36 | 8.65 (d, J = 7.2 Hz, 1H), 7.23 (d, J = 11.2 Hz, 1H), 7.14 (d, J = 2.4 Hz, 1H), 3.12-3.14 (m, 2H), 2.76 (s, 3H), 1.76-1.82 (m, 2H), 1.04 (t, J = 7.6 Hz, 3H) |
| 38 | 8.15 (d, J = 6.8 Hz, 1H), 7.18 (d, J = 10.0 Hz, 1H), 3.44-3.54 (m, 2H), 2.49 (s, 3H), 2.14 (d, J = 2.0 Hz, 3H) |
| 40 | 7.65-7.68 (m, 3H), 7.50 (m, 3H), 7.21 (s, 1H), 6.68 (s, 1H), 3.38 (q, J = 9.6 Hz, 2H), 2.51 (s, 3H), 2.46 (s, 3H) |
| 41 | 8.03 (s, 1H), 7.63-7.65 (m, 2H), 7.49-7.56 (m, 3H), 7.23 (s, 1H), 6.71 (s, 1H), 3.38-3.49 (m, 2H), 2.56 (s, 3H), 2.41 (s, 3H) |
| 42 | 8.21 (s, 1H), 7.64-7.66 (m, 2H), 7.49-7.55 (m, 3H), 7.34 (s, 1H), 6.71 (s, 1H), 3.93 (q, J = 8.8 Hz, 2H), 2.71 (s, 3H), 2.58 (s, 3H) |
| 43 | 7.87 (s, 1H), 7.40 (s, 1H), 7.12 (s, 1H), 3.44 (q, J = 9.6 Hz, 2H), 2.50 (s, 3H) |
| 44 | 8.34 (s, 1H), 7.47 (s, 1H), 7.10 (s, 1H), 3.40-3.52 (m, 2H), 2.46 (s, 3H) |
| 45 | 8.43 (s, 1H), 7.58 (s, 1H), 7.12 (s, 1H), 3.97 (q, J = 8.8 Hz, 2H), 2.76 (s, 3H) |
| 46 | 7.64 (s, 1H), 7.20 (s, 1H), 6.81 (t, J = 53.6 Hz, 1H), 6.75 (s, 1H), 3.37 (q, J = 9.6 Hz, 2H), 2.50 (s, 3H), 2.44 (s, 3H) |
| 47 | 8.06 (s, 1H), 7.25 (d, J = 5.6 Hz, 1H), 6.85 (s, 1H), 6.82 (t, J = 53.6 Hz, 1H), 3.39-3.47 (m, 2H), 2.55 (s, 3H), 2.42 (s, 3H) |
| 48 | 8.15 (s, 1H), 7.36 (s, 1H), 6.83 (t, J = 54.0 Hz, 1H), 6.82 (s, 1H), 3.94 (q, J = 8.8 Hz, 2H), 2.72 (s, 3H), 2.59 (s, 3H) |
| 49 | 7.65 (s, 1H), 7.21 (s, 1H), 6.80 (s, 1H), 3.37 (q, J = 10.0 Hz, 2H), 2.50 (s, 3H), 2.46 (s, 3H) |
| 50 | 8.06 (s, 1H), 7.26 (s, 1H), 6.92 (s, 1H), 3.40-3.49 (m, 2H), 2.58 (s, 3H), 2.42 (s, 3H) |
| 51 | 8.15 (s, 1H), 7.37 (s, 1H), 6.89 (s, 1H), 3.95 (q, J = 8.8 Hz, 2H), 2.73 (s, 3H), 2.61 (s, 3H) |
| 52 | 7.84 (s, 1H), 7.63-7.65 (m, 2H), 7.48-7.55 (m, 3H), 7.37 (s, 1H), 6.96 (s, 1H), 3.43 (q, J = 9.6 Hz, 2H), 2.48 (s, 3H) |

TABLE 2-continued

Detail and $^1$H-NMR of the compounds synthesized belonging to the Formula (I) of the present invention:

| No. | $^1$H-NMR δppm (CDCl$_3$/TMS) |
|---|---|
| 53 | 8.29 (s, 1H), 7.62-7.64 (m, 2H), 7.50-7.52 (m, 3H), 7.44 (s, 1H), 6.93 (s, 1H), 3.41-3.53 (m, 2H), 2.44 (s, 3H) |
| 54 | 8.39 (s, 1H), 7.63-7.65 (m, 2H), 7.49-7.55 (m, 4H), 6.95 (s, 1H), 3.94 (q, J = 8.8 Hz, 2H), 2.74 (s, 3H) |
| 55 | 7.86 (s, 1H), 7.39 (s, 1H), 7.06 (s, 1H), 6.82 (t, J = 53.6 Hz, 1H), 3.44 (q, J = 9.6 Hz, 2H), 2.50 (s, 3H) |
| 56 | 8.33 (s, 1H), 7.46 (s, 1H), 7.05 (s, 1H), 6.83 (t, J = 53.6 Hz, 1H), 3.42-3.54 (m, 2H), 2.45 (s, 3H) |
| 57 | 8.42 (s, 1H), 7.57 (s, 1H), 7.06 (s, 1H), 6.83 (t, J = 53.6 Hz, 1H), 3.96 (q, J = 8.8 Hz, 2H), 2.75 (s, 3H) |

Formulation Example 1: Emulsions 10 parts of each compound of the invention was dissolved in 45 parts of Solvesso® 150 and 35 parts of N-methylpyrrolidone. 10 parts of an emulsifier (trade name: Sorpol® 3005X, produced by Toho Chemical Industry Co., Ltd.) was added thereto. The mixtures were mixed by stirring to give 10% emulsions.

Formulation Example 2: Wettable Powders 20 parts of each compound of the invention was added to a mixture of 2 parts of sodium lauryl sulfate, 4 parts of sodium lignin sulfonate, 20 parts of fine powder of synthetic hydrated silicon dioxide, and 54 parts of clay. The mixtures were mixed by stirring with a juice mixer to give 20% wettable powders.

Formulation Example 3: Granules 2 parts of sodium dodecylbenzenesulfonate, 10 parts of bentonite, and 83 parts of clay were added to 5 parts of each compound of the invention, and each mixture was sufficiently mixed by stirring. An appropriate amount of water was added thereto. The resulting mixtures were further stirred and granulated with a granulator. The granules were air-dried to give 5% granules.

Formulation Example 4: Dusts 1 part of each compound of the invention was dissolved in an appropriate amount of acetone. 5 parts of fine powder of synthetic hydrated silicon dioxide, 0.3 parts of acidic isopropyl phosphate (PAP), and 93.7 parts of clay were added thereto. The mixtures were mixed by stirring with a juice mixer, and acetone was removed by evaporation to give 1% dust.

Formulation Example 5: Flowable preparations 20 parts of each compound of the invention was mixed with 20 parts of water containing 3 parts of polyoxyethylene tristyrylphenyl ether phosphoric acid ester triethanolamine and 0.2 parts of Rhodorsil® 426R. The mixtures were subjected to wet pulverization with a DYNO-Mill, and mixed with 60 parts of water containing 8 parts of propylene glycol and 0.32 parts of xanthan gum to give 20% suspensions in water.

Test Examples are given below to demonstrate that the compounds of the invention are useful as an active ingredient for miticides and nematocides.

The compound A was the representative compound mentioned in the specification of JP2008-308448A. This compound A was identical with the compound of [Mb] No. 2-1.

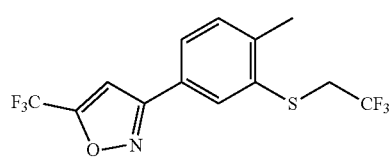

[I-Ib]No. 2-1

Test Example 1 (Miticidal Test on Two-Spotted Spider Mite)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm) was then placed on the sufficiently soaked, non-woven fabric. Another kidney bean leaf with two-spotted spider mites (about 30 mite samples) was placed on top of the first leaf, and the fabric and leaves were placed in a thermostatic chamber having a temperature of 25±2° C. and a humidity of 40% overnight. Next morning the top leaf was removed as the mite population had already moved to the lower leaf.

Miticidal formulations containing the compound of the invention (100 ppm and 5 ppm) were prepared by adding an aqueous solution (100 ppm) of Sorpol 355 (manufactured by Tobo Kagaku Co., Ltd.) to a methanol solution of the compound of the invention. These miticidal formulations were sprayed onto the leaves, and the leaves were air-dried and placed in a thermostatic chamber (25±2° C. and a humidity of 50%). The mortality rate of the two-spotted spider mites was calculated after 2 days. The results of this test are shown in Table 3:

TABLE 3

| | Mortality of mites (%) | |
|---|---|---|
| No. | 100 ppm | 5 ppm |
| 1 | 100 | 30 |
| 2 | 100 | 100 |
| 4 | 100 | 20 |
| 5 | 100 | 95 |
| 8 | 100 | 100 |
| 11 | 100 | 68 |
| 13 | 100 | 48 |
| 14 | 100 | 40 |
| 17 | 100 | 98 |
| 19 | 100 | 100 |
| 20 | 100 | 93 |
| 22 | 100 | 73 |
| 23 | 100 | 100 |
| 25 | 100 | 10 |
| 26 | 100 | 98 |
| 32 | 100 | 18 |

TABLE 3-continued

| | Mortality of mites (%) | |
|---|---|---|
| No. | 100 ppm | 5 ppm |
| 34 | 100 | 0 |
| 35 | 100 | 100 |
| 38 | 100 | 100 |
| 40 | 100 | 33 |
| 43 | 100 | 100 |
| 44 | 100 | 100 |
| 46 | 100 | 79 |
| 47 | 100 | 51 |
| 49 | 100 | 6 |
| 50 | 100 | 96 |
| 52 | 100 | 61 |
| 53 | 100 | 64 |
| 55 | 100 | 100 |
| 56 | 100 | 100 |
| Compound A | 100 | 0 |

The compounds (from Table 3) that exhibited the mortality rate of 100% at 5 ppm are as follows: Compound Nos.: 2, 8, 19, 23, 35, 38, 43, 44, 55 and 56.

Test Example 2 (Ovicidal Test on Two-Spotted Spider Mites)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm) was then placed on the sufficiently soaked, non-woven fabric. Twenty female adults of two-spotted spider mite were placed on the top of the leaf, and the fabric and leaf were placed in a thermostatic chamber having a temperature of 25±2° C. and a humidity of 40% and 16L8D.

The next day, after the number of the female adults was adjusted once more to 20, 2 mL of a miticidal formulation containing the compound of the invention (10 ppm) prepared in the same manner as in test example 1 was sprayed onto the leaf, and the leaf was air-dried and placed in a thermostatic chamber (25±2° C. and a humidity of 50%). The ovicidal rate of the two-spotted spider mites was calculated 6 days after the spraying of the miticidal formulation. The results of this test are shown in Table 4:

TABLE 4

| No. | Ovicidal activity (%) 10 ppm |
|---|---|
| 2 | 100 |
| 5 | 90 |
| 8 | 90 |
| 11 | 50 |
| 13 | 98 |
| 14 | 50 |
| 17 | 100 |
| 19 | 100 |
| 20 | 95 |
| 23 | 100 |
| 26 | 90 |
| 32 | 36 |
| 35 | 100 |
| 38 | 100 |
| 40 | 89 |
| 43 | 100 |
| 44 | 100 |
| 46 | 83 |
| 47 | 80 |
| 49 | 0 |
| 50 | 97 |
| 52 | 32 |
| 53 | 90 |

TABLE 4-continued

| No. | Ovicidal activity (%) 10 ppm |
|---|---|
| 55 | 100 |
| 56 | 100 |
| Compound A | 0 |

The compounds (from Table 4) that exhibited the mortality rate of 100% at 10 ppm are as follows:
Compound Nos.: 2, 17, 19, 23, 35, 38, 43, 44, 55 and 56.
The compounds (from Tables 3 and 4) that exhibited the mortality rate of 100% at 5 ppm in Table 3 and 100% at 10 ppm in Table 4 are as follows:
Compound Nos.: 2, 19, 23, 35, 38, 43, 44, 55 and 56.

Test Example 3 (Miticidal Test on Two-Spotted Spider Mites (Systemic Activity))

10 mL of Test compound solution is drenched to kidney bean pot (6.5 cm diameter and 6.5 cm height) eight days after sowing at 10 mg a.i./pot. After application, plants are placed in green house having a temperature of 25±2° C. After 5 days, a kidney bean leaf from treated pot (about 3.5×4.5 cm) was then placed on the sufficiently soaked, non-woven fabric. Two-spotted spider mites (about 30 mite samples) were placed on the leaf, and the cups are placed in a thermostatic chamber having a temperature of 25±2° C. The mortality rate of the adult two-spotted spider mites was calculated after 2 days. The compounds that exhibited the mortality rate of 50% or more are as follows:
Compound Nos.: 2, 16, 17, 23, 35, 43, 44 and 49.

Test Example 4 (Nematocidal Test on Root-Knot Nematodes)

1 mL of test compound with desired concentration (40 ppm) and 1 mL nematode suspension (500 nematode/mL) were added to wide mouth glass vial filled $2/3^{rd}$ with sea sand (8 g). Vial mouth was sealed with stretched parafilm and pierced at center. 2-3 weeks old Tomato plant was cut from stem and inserted into the test vial. Vials were kept in a thermostatic chamber having a temperature of 25±2° C. After two weeks, plants were carefully removed from vial and assessed for root knot nodules. The assessment was done on the basis of score of 0-4 (0 is no infestation; 4 is 100% infestation). Damage degree of the root knot was judged according to the index shown in Table 5:

TABLE 5

| Index of Root-knot | Degree of root-knot formation |
|---|---|
| 4 | countless knots were observed and roots growth were inhibited |
| 3 | many knot were observed in whole roots |
| 2 | knots were observed |
| 1 | prominent knots were observed |
| 0 | no knots were observed |

The compounds those who exhibited root-knot nodular index 1 or less were as follows:
Compound Nos.: 2, 5, 9, 10, 13, 14, 17, 19, 20, 23, 25, 27, 29, 31, 35, 38, 40, 43, 44, 46, 49, 50, 55 and 56.
(Note)

As described above, the present invention is illustrated by preferable embodiments of the present invention. However, it will be understood that the scope of the present invention should be interpreted only by the claims. It is understood that patents, patent applications and literatures cited herein are incorporated herein by reference, as if the contents thereof are specifically described herein. The present application claims priority to Indian Patent Application No.

201711042933 filed on Nov. 30, 2017 with the Indian Patent Office (Intellectual Property India), the entire content of which is incorporated herein by reference.

INDUSTRIAL APPLICABILITY

The isoxazole compound of the present invention shows an excellent controlling effect against a wide range of pests such as mites and plant parasitic nematodes and is useful as a miticide or nematocidal agent for agricultural and horticultural use.

We claim:
1. An isoxazole compound represented by Formula (I):

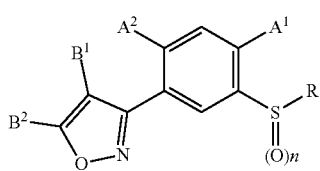

or a salt thereof,
wherein
R represents $C_{1-6}$ alkyl, or $C_{1-4}$ haloalkyl;
$A^1$ and $A^2$ are identical or different and each halogen or $C_{1-6}$ alkyl;
$B^1$ represents hydrogen, halogen or $C_{1-6}$ alkyl;
$B^2$ represents $C_{1-6}$ alkyl, $C_{1-4}$ haloalkyl, or substituted or unsubstituted aryl $C_{1-4}$ haloalkyl; and
n represents an integer of 0 to 2.

2. The isoxazole compound or the salt thereof according to claim 1, wherein R is normal propyl or 2,2,2-trifluoroethyl.

3. The isoxazole compound or the salt thereof according to claim 1, wherein $A^1$ is fluorine, chlorine, or methyl.

4. The isoxazole compound or the salt thereof according to claim 1, wherein $A^2$ is fluorine, chlorine, or methyl.

5. The isoxazole compound or the salt thereof according to claim 1, wherein $B^1$ is hydrogen or methyl.

6. The isoxazole compound or the salt thereof according to claim 1, wherein $B^2$ is difluoromethyl, trifluoromethyl, chlorodifluoromethyl, pentafluoroethyl, heptafluoropropyl or difluoro(phenyl)methyl.

7. The isoxazole compound or the salt thereof according to claim 1, wherein n is an integer of 0 or 1.

8. The isoxazole compound or the salt thereof according to claim 1, which is selected from the group consisting of:
3-(2-fluoro-4-methyl-5-((2,2,2-trifluoroethyl)sulfinyl)phenyl)-5-(trifluoromethyl)isoxazole
3-(2-fluoro-4-methyl-5-((2,2,2-trifluoroethyl)sulfinyl)phenyl)-5-(heptafluoropropyl)isoxazole;
5-(difluoromethyl)-3-(2-fluoro-4-methyl-5-((2,2,2-trifluoroethyl)thio)phenyl)isoxazole;
5-(chlorodifluoromethyl)-3-(2-fluoro-4-methyl-5-((2,2,2-trifluoroethyl)sulfinyl)phenyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole
3-(2,4-dimethyl-5-((2,2,2-trifluoroethyl)sulfinyl)phenyl)-5-(trifluoromethyl)isoxazole;
3-(2-fluoro-4-methyl-5-(propyl sulfinyl)phenyl)-5-(trifluoromethyl)isoxazole;
3-(2-fluoro-4-methyl-5-((2,2,2-trifluoroethyl)sulfinyl)phenyl)-4-methyl-5-(trifluoromethyl)isoxazole;
3-(2-chloro-4-methyl-5-((2,2,2-trifluoroethyl)thio)phenyl)-5-(chlorodifluoromethyl)isoxazole;
3-(2-chloro-4-methyl-5-((2,2,2-trifluoroethyl)sulfinyl)phenyl)-5-(chlorodifluoromethyl)isoxazole;
5-(difluoromethyl)-3-(2,4-dimethyl-5-((2,2,2-trifluoroethyl)thio)phenyl)isoxazole;
5-(difluoromethyl)-3-(2,4-dimethyl-5-((2,2,2-trifluoroethyl)sulfinyl)phenyl)isoxazole;
5-(chlorodifluoromethyl)-3-(2,4-dimethyl-5-((2,2,2-trifluoroethyl)thio)phenyl)isoxazole;
5-(chlorodifluoromethyl)-3-(2,4-dimethyl-5-((2,2,2-trifluoroethyl)sulfinyl)phenyl)isoxazole;
3-(2-chloro-4-methyl-5-((2,2,2-trifluoroethyl)thio)phenyl)-5-(difluoro(phenyl)methyl)isoxazole;
3-(2-chloro-4-methyl-5-((2,2,2-trifluoroethyl)sulfinyl)phenyl)-5-(difluoro(phenyl)methyl)isoxazole;
3-(2-chloro-4-methyl-5-((2,2,2-trifluoroethyl)thio)phenyl)-5-(difluoromethyl)isoxazole; and
3-(2-chloro-4-methyl-5-((2,2,2-trifluoroethyl)sulfinyl)phenyl)-5-(difluoromethyl)isoxazol.

9. The isoxazole compound or the salt thereof according to claim 1, which is selected from the group consisting of:
3-(2-fluoro-4-methyl-5-((2,2,2-trifluoroethyl)sulfinyl)phenyl)-5-(trifluoromethyl)isoxazole;
3-(2-fluoro-4-methyl-5-((2,2,2-trifluoroethyl)sulfinyl)phenyl)-5-(heptafluoropropyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole;
3-(2-fluoro-4-methyl-5-(propyl sulfinyl)phenyl)-5-(trifluoromethyl)isoxazole;
3-(2-fluoro-4-methyl-5-((2,2,2-trifluoroethyl)sulfinyl)phenyl)-4-methyl-5-(trifluoromethyl)isoxazole;
3-(2-chloro-4-methyl-5-((2,2,2-trifluoroethyl)thio)phenyl)-5-(chlorodifluoromethyl)isoxazole;
3-(2-chloro-4-methyl-5-((2,2,2-trifluoroethyl)sulfinyl)phenyl)-5-(chlorodifluoromethyl)isoxazole;
3-(2-chloro-4-methyl-5-((2,2,2-trifluoroethyl)thio)phenyl)-5-(difluoromethyl)isoxazole; and
3-(2-chloro-4-methyl-5-((2,2,2-trifluoroethyl)sulfinyl)phenyl)-5-(difluoromethyl)isoxazole.

10. The isoxazole compound or the salt thereof according to claim 1, which is selected from the group consisting of:
3-(2-fluoro-4-methyl-5-((2,2,2-trifluoroethyl)sulfinyl)phenyl)-5-(trifluoromethyl)isoxazole;
5-(chlorodifluoromethyl)-3-(2-fluoro-4-methyl-5-((2,2,2-trifluoroethyl)sulfinyl)phenyl)isoxazole;
5-(difluoro(phenyl)methyl)-3-(2-fluoro-4-methyl-5-((2,2,2-trifluoroethyl)thio)phenyl)isoxazole;
3-(2-chloro-4-methyl-5-((2,2,2-trifluoroethyl)sulfinyl)phenyl)-5-(trifluoromethyl)isoxazole;
3-(2-fluoro-4-methyl-5-(propyl sulfinyl)phenyl)-5-(trifluoromethyl)isoxazole;
3-(2-fluoro-4-methyl-5-((2,2,2-trifluoroethyl)sulfinyl)phenyl)-4-methyl-5-(trifluoromethyl)isoxazole;
3-(2-chloro-4-methyl-5-((2,2,2-trifluoroethyl)thio)phenyl)-5-(chlorodifluoromethyl)isoxazole;
3-(2-chloro-4-methyl-5-((2,2,2-trifluoroethyl)sulfinyl)phenyl)-5-(chlorodifluoromethyl)isoxazole;
3-(2-chloro-4-methyl-5-((2,2,2-trifluoroethyl)thio)phenyl)-5-(difluoromethyl)isoxazole; and
3-(2-chloro-4-methyl-5-((2,2,2-trifluoroethyl)sulfinyl)phenyl)-5-(difluoromethyl)isoxazole.

11. The isoxazole compound or the salt thereof according to claim 1, which is selected from the group consisting of:
- 3-(2-fluoro-4-methyl-5-((2,2,2-trifluoroethyl)sulfinyl)phenyl)-5-(trifluoromethyl)isoxazole;
- 5-(difluoro(phenyl)methyl)-3-(2-fluoro-4-methyl-5-((2,2,2-trifluoroethyl)thio)phenyl)isoxazole;
- 3-(2-chloro-4-methyl-5-((2,2,2-trifluoroethyl)sulfinyl)phenyl)-5-(trifluoromethyl)isoxazole;
- 3-(2-fluoro-4-methyl-5-(propyl sulfinyl)phenyl)-5-(trifluoromethyl)isoxazole;
- 3-(2-fluoro-4-methyl-5-((2,2,2-trifluoroethyl)sulfinyl)phenyl)-4-methyl-5-(trifluoromethyl)isoxazole;
- 3-(2-chloro-4-methyl-5-((2,2,2-trifluoroethyl)thio)phenyl)-5-(chlorodifluoromethyl)isoxazole;
- 3-(2-chloro-4-methyl-5-((2,2,2-trifluoroethyl)sulfinyl)phenyl)-5-(chlorodifluoromethyl)isoxazole;
- 3-(2-chloro-4-methyl-5-((2,2,2-trifluoroethyl)thio)phenyl)-5-(difluoromethyl)isoxazole; and
- 3-(2-chloro-4-methyl-5-((2,2,2-trifluoroethyl)sulfinyl)phenyl)-5-(difluoromethyl)isoxazole.

12. A pest controlling agent comprising as an active ingredient the isoxazole compound or the salt thereof according to claim 1.

13. An agricultural composition comprising the isoxazole compound or the salt thereof according to claim 1.

14. A composition for controlling a pest, comprising the isoxazole compound or the salt thereof according to claim 1.

15. A miticidal composition comprising the isoxazole compound or the salt thereof according to claim 1.

16. An ovicidal composition comprising the isoxazole compound or the salt thereof according to claim 1.

17. A nematocidal composition comprising the isoxazole compound or the salt thereof according to claim 1.

18. A method for controlling pests comprising using the isoxazole compound or the salt thereof according to claim 1.

19. A method for controlling pests, comprising applying the isoxazole compound or the salt thereof according to claim 1 to a plant or its vicinity, or soil where a plant is cultivated.

20. A method for controlling pests, comprising applying an effective amount of the isoxazole compound or the salt thereof according to claim 1 to pests, a habitat of pests, or a place where inhabitation by pests is predicted.

21. A method for killing a mite, comprising applying the isoxazole compound or the salt thereof according to claim 1 to a plant or its vicinity, or soil where a plant is cultivated.

22. A method for killing a mite, comprising applying an effective amount of the isoxazole compound or the salt thereof according to claim 1 to a mite, a habitat of mites, or a place where inhabitation by mites is predicted.

23. A method for killing an ovum, comprising applying the isoxazole compound or the salt thereof according to claim 1 to a plant or its vicinity, or soil where a plant is cultivated.

24. A method for killing an ovum, comprising applying an effective amount of the isoxazole compound or the salt thereof according to claim 1 to an ovum or a place where oviposition is predicted.

25. A method for killing a nematode, comprising applying the isoxazole compound or the salt thereof according to claim 1 to a plant or its vicinity, or soil where a plant is cultivated.

26. A method for killing a nematode, comprising applying an effective amount of the isoxazole compound or the salt thereof according to claim 1 to a nematode, a habitat of nematodes, or a place where inhabitation by a nematode is predicted.

27. The isoxazole compound or the salt thereof according to claim 1, wherein
R is normal propyl or 2,2,2-trifluoroethyl;
$A^1$ is fluorine, chlorine, or methyl; and
$A^2$ is fluorine, chlorine, or methyl.

28. The isoxazole compound or the salt thereof according to claim 1, wherein
R is normal propyl or 2,2,2-trifluoroethyl;
$A^1$ is fluorine, chlorine, or methyl;
$A^2$ is fluorine, chlorine, or methyl;
$B^1$ is hydrogen or methyl;
$B^2$ is difluoromethyl, trifluoromethyl, chlorodifluoromethyl, pentafluoroethyl, heptafluoropropyl or difluoro(phenyl)methyl; and
n is an integer of 0 or 1.

* * * * *